(12) United States Patent
Davis et al.

(10) Patent No.: US 10,765,839 B2
(45) Date of Patent: Sep. 8, 2020

(54) INFLATION DEVICE WITH DETACHABLE HOUSING AND RELATED METHODS

(71) Applicant: Merit Medical Systems, Inc., South Jordan, UT (US)

(72) Inventors: Jon Davis, Sandy, UT (US); Prasad Weerakoon, Provo, UT (US); Russell D. Heyborne, Riverton, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 655 days.

(21) Appl. No.: 15/469,082

(22) Filed: Mar. 24, 2017

(65) Prior Publication Data

US 2017/0274191 A1    Sep. 28, 2017

Related U.S. Application Data

(60) Provisional application No. 62/314,014, filed on Mar. 28, 2016.

(51) Int. Cl.
*A61M 25/10* (2013.01)
*A61M 16/00* (2006.01)
*A61M 16/04* (2006.01)

(52) U.S. Cl.
CPC ........ *A61M 25/10182* (2013.11); *A61M 25/10188* (2013.11); *A61M 16/044* (2013.01); *A61M 2016/0027* (2013.01); *A61M 2205/073* (2013.01); *A61M 2205/3331* (2013.01); *A61M 2205/502* (2013.01); *A61M 2205/8206* (2013.01)

(58) Field of Classification Search
CPC .......... A61M 25/10182; A61M 25/10188
See application file for complete search history.

(56) References Cited

U.S. PATENT DOCUMENTS

| | | | |
|---|---|---|---|
| 5,449,344 A * | 9/1995 | Taylor | A61M 25/10182 604/100.03 |
| 5,449,345 A * | 9/1995 | Taylor | G01D 9/00 604/100.03 |
| 6,958,053 B1 | 10/2005 | Reilly | |
| 20,070,112 | 5/2007 | Smit et al. | |
| 7,824,374 B2 | 11/2010 | Niehoff | |
| 2005/0004518 A1 | 1/2005 | Call | |
| 2010/0217188 A1* | 8/2010 | Lampropoulos | A61M 25/10184 604/97.03 |

(Continued)

FOREIGN PATENT DOCUMENTS

| | | |
|---|---|---|
| WO | 2010075083 | 7/2010 |
| WO | 2017007797 | 1/2017 |

OTHER PUBLICATIONS

International Search Report and Written Opinion dated Jul. 3, 2017 for PCT/US2017/024060.
European Search Report dated Nov. 7, 2019 for EP17776356.2.

*Primary Examiner* — Jenna Zhang
(74) *Attorney, Agent, or Firm* — Stoel Rives LLP

(57) ABSTRACT

A syringe assembly or inflation device that includes a detachable housing. A pressure-sensing syringe assembly or inflation device can include both a syringe barrel and a housing that is coupled to the syringe barrel in a locked configuration. The inflation device can transition from the locked configuration to the unlocked configuration in which the housing is separable from the syringe barrel. Related methods are also disclosed.

19 Claims, 24 Drawing Sheets

(56) References Cited

U.S. PATENT DOCUMENTS

2013/0047395 A1\* 2/2013 Lampropolous ............................ A61M 25/10182
29/407.01
2017/0007806 A1\* 1/2017 Weerakoon ..... A61M 25/10188

\* cited by examiner

INFLATION DEVICE WITH DETACHABLE HOUSING AND RELATED METHODS

RELATED APPLICATIONS

This application claims priority to U.S. Provisional Application No. 62/314,014, filed on Mar. 28, 2016 and titled "Inflation Device with Detachable Housing and Related Methods," which is hereby incorporated by reference in its entirety.

TECHNICAL FIELD

The present disclosure relates generally to the field of medical devices. More particularly, some embodiments of the disclosure are directed to inflation devices or syringe assemblies that include a detachable housing. Related components and methods are also disclosed.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

This disclosure broadly relates to syringe assemblies, inflation devices, and related components and methods for pressurizing, depressurizing, and/or otherwise displacing fluid. Certain embodiments relate, more particularly, to syringe assemblies that include a detachable housing.

A detachable housing of a syringe assembly may enclose one or more components (e.g., a display screen, a circuit board, a power source) that facilitate the measurement of pressure within a syringe barrel of a syringe assembly. While some components of a syringe assembly (e.g., the syringe barrel) may be designed for single use, other components of the syringe assembly (e.g., the display screen and/or the circuit board) may be suitable for multiple uses. A syringe assembly with a detachable housing allows the syringe barrel to be discarded after a single use, while allowing the housing and/or one or more components disposed therein to be reused and/or repackaged for further use.

The components of the embodiments as generally described and illustrated in the figures herein can be arranged and designed in a wide variety of configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities, including mechanical and fluidic interaction. Two components may be coupled to each other even though they are not in direct contact with each other. The phrase "attached to" refers to interaction between two or more entities which are in direct contact with each other and/or are separated from each other only by a fastener (e.g., adhesives, screws) of any suitable variety. The phrase "fluid communication" refers to arrangements in which a fluid, such as a gas or a liquid, can flow from one element to another element when the elements are in fluid communication with each other.

The terms "proximal" and "distal" are opposite directional terms. For example, the distal end of a device or component is the end of the component that is furthest from the practitioner during ordinary use. The proximal end refers to the opposite end, or the end nearest the practitioner during ordinary use.

Figure 1:
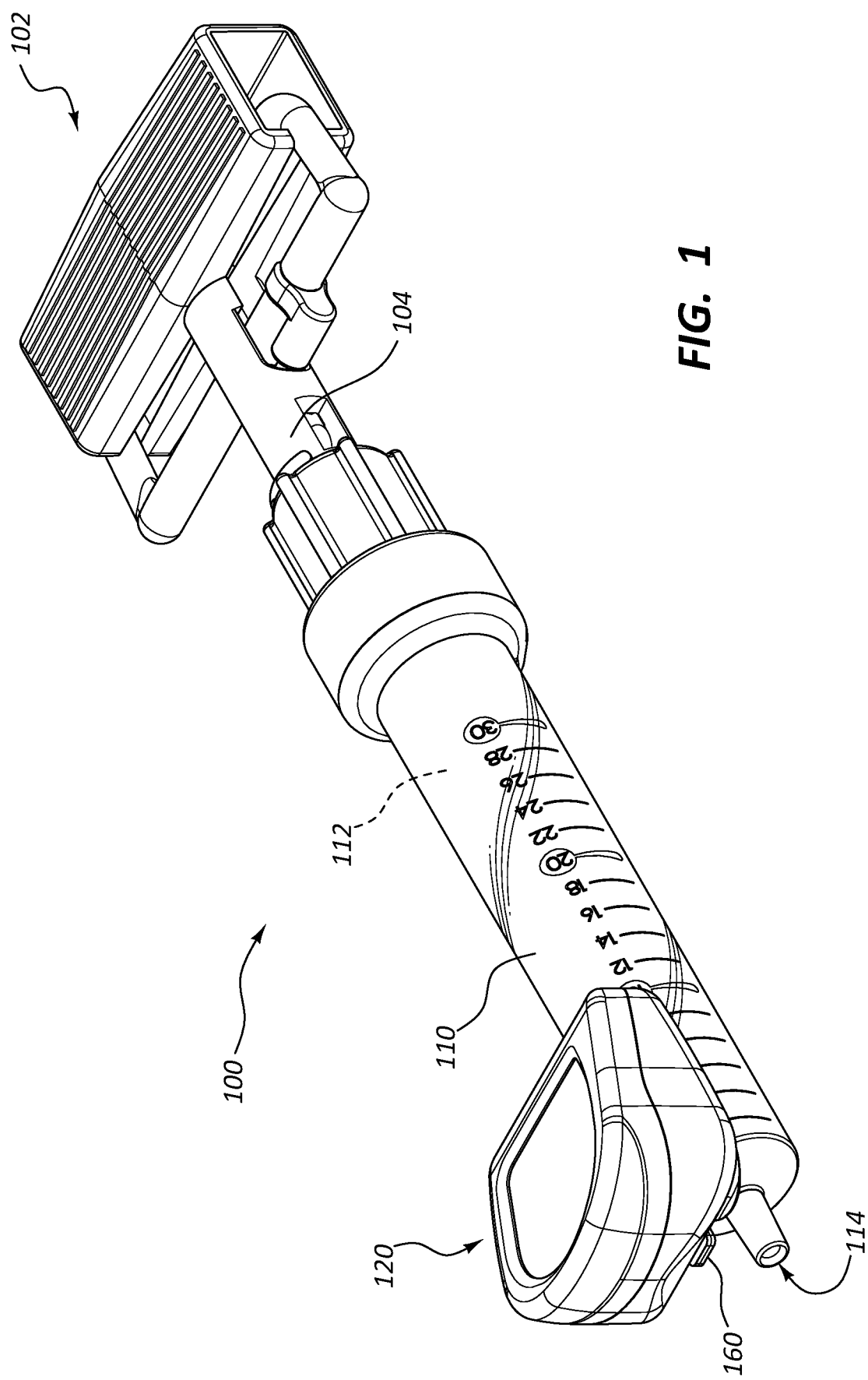
FIG. 1 is a perspective view of a syringe assembly.
Figure 2:
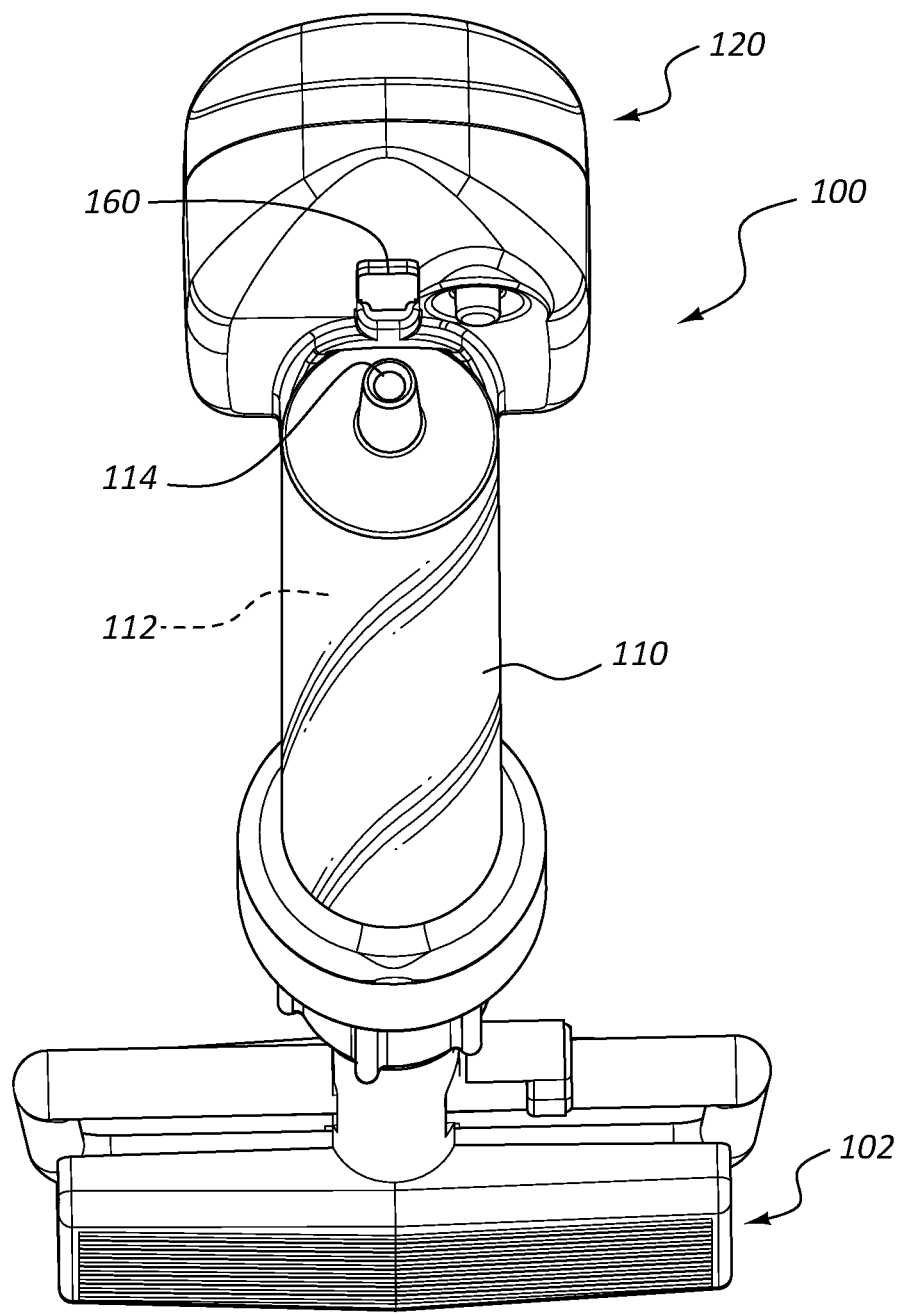
FIG. 2 is an alternative perspective view of the syringe assembly of FIG. 1.

FIGS. 1-14 provide various views of a syringe assembly 100 (e.g., an inflation device) or portions thereof. For example, FIGS. 1 and 2 provide alternative perspective views of the syringe assembly 100. As shown in these figures, the syringe assembly 100 includes, among other elements, a handle 102, a plunger 104, an elongate syringe barrel 110, and a housing 120. In the depicted embodiment, the handle 102 is coupled to the proximal end of the plunger 104. The plunger 104 may be configured to be disposed within the syringe barrel 110 such that advancement of the plunger 104 within the syringe barrel 110 causes displacement of fluid that is disposed within a fluid reservoir 112 of the syringe barrel 110. In some embodiments, the plunger 104 is configured to selectively couple to the syringe barrel 110 via a plurality of threads (not shown). In further embodiments, the handle 102 includes one or more elements that are designed to provide mechanical advantage in coupling and/or decoupling the plunger 104 to the syringe barrel 110.

The syringe assembly 100 may be used to inflate and/or pressurize a medical appliance or some other pressurizable element (such as an invertebral disc), inject or withdraw fluid from a medical device or patients body, and so forth. In some embodiments, the syringe assembly 100 may be used to inflate a medical appliance, such as a balloon catheter (not shown). More particularly, a distal port 114 of the syringe barrel 110 may be connected to a balloon catheter. When the plunger 104 is advanced within the syringe barrel 110, fluid may be forced from the fluid reservoir 112 of the syringe barrel 110 through the distal port 114 into the balloon catheter, thereby inflating the balloon of the balloon catheter. The syringe assembly 100 may be used in an analogous manner to inflate other medical appliances. In other instances, the syringe assembly 100 may be used to pressurize some other element, such as an invertebral disc in a lumbar provocative discography procedure.

As shown in FIGS. 1 and 2, the syringe assembly 100 includes a housing 120 that is configured to couple to the syringe barrel 110. The housing 120 may enclose or surround one or more components of the syringe assembly 100 to facilitate the measurement of pressure within the syringe barrel 110 during a medical procedure.

In some embodiments, the syringe assembly 100 may include a key 160 that is configured to facilitate detachment of the housing 120 from the syringe barrel 110. In some embodiments, at least a portion of the key 160 may extend distally from the housing, thereby allowing a practitioner to push (e.g., exert a proximal force on) the key 160 to transition the syringe assembly 100 from a locked configuration that prevents movement of the syringe barrel 110 relative to the housing 120 to an unlocked configuration in which the syringe barrel 110 is free to move relative to the housing 120. Both the key 160 and the mechanism for transitioning the syringe assembly 100 from a locked configuration to an unlocked configuration are described in greater detail below.

Figure 3:
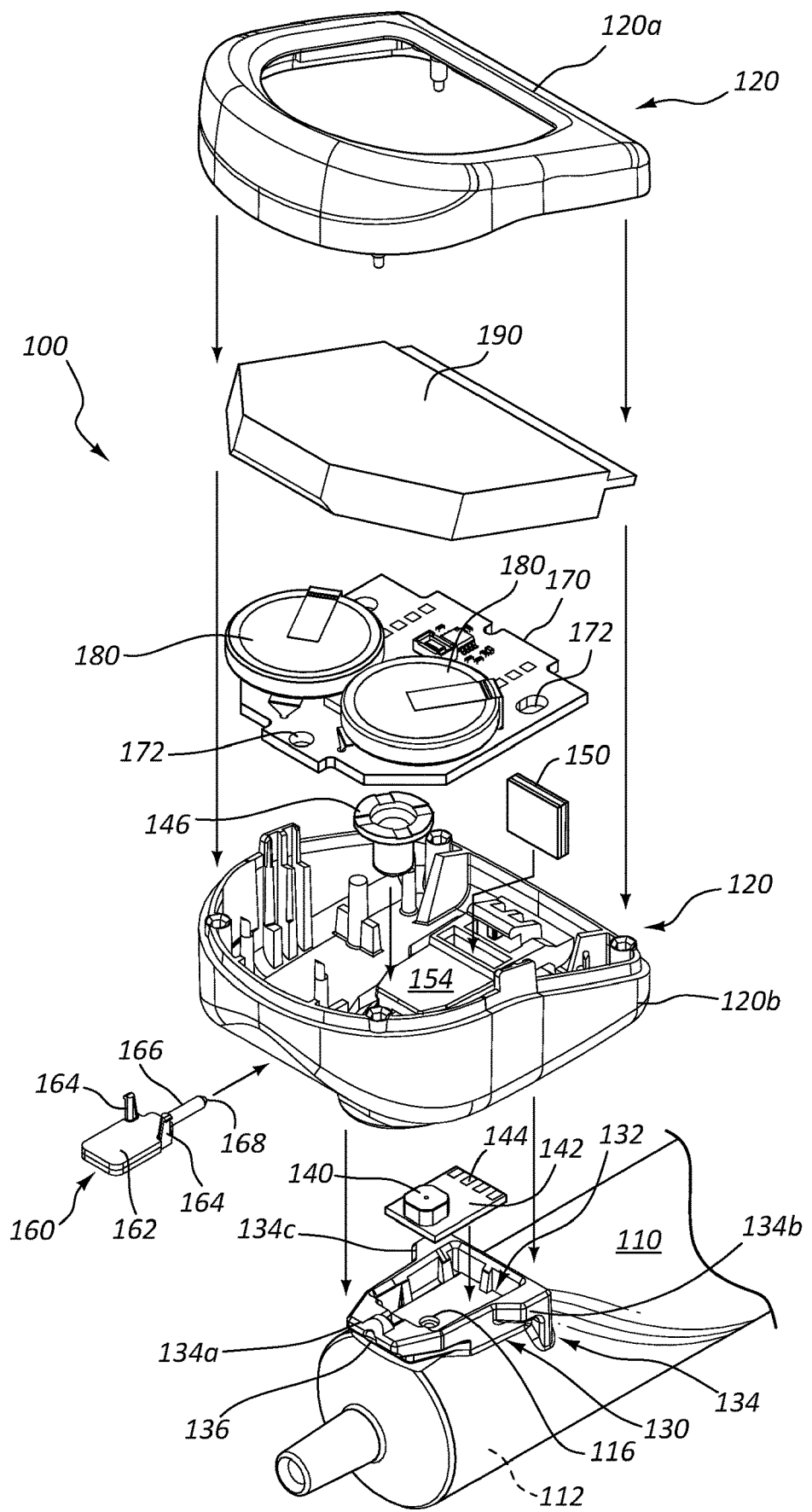
FIG. 3 is an exploded perspective view of a distal portion of the syringe assembly of FIG. 1.

FIG. 3 provides an exploded perspective view of a portion of the syringe assembly 100. More particularly, FIG. 3 shows, among other things, a distal portion of the syringe barrel 110, an aperture 116 that extends through a wall of the syringe barrel 110, an adaptor 130 that is coupled to the syringe barrel 110, a lower portion of the housing 120b that is configured to couple to the syringe barrel 110 via the adaptor 130, a pressure transducer 140 that is coupled to a base plate 142, a key 160, an elastomeric connector 150, an actuator 146, a circuit board 170 having a plurality of holes 172, a power source 180, a display screen 190, and an upper portion of the housing 120a. When assembled, the pressure transducer 140, the elastomeric connector 150, the circuit board 170, and the display screen 190 may be in electrical communication with one another.

As shown in FIG. 3, the aperture 116 and the adaptor 130 may be disposed adjacent a distal end of the syringe barrel 110. The adaptor 130 may be attached or otherwise coupled to the syringe barrel 110 in any suitable manner. For example, the adaptor 130 may be integrally formed with the syringe barrel 110, welded to the syringe barrel 110, or attached to the syringe barrel 110 via an adhesive.

In the depicted embodiment, the adaptor 130 includes a plurality of flanges 134a, 134b, 134c. For instance, the depicted embodiment includes a distal flange 134a that extends distal of a lower portion of the adaptor 130 and two proximal flanges 134b, 134c that extend lateral of the lower portion of the adaptor 130. Each of the flanges 134a, 134b, 134c includes a lower surface that is configured to contact the upper surface of the lower portion of the housing 120b. The adaptor 130 may further include a channel 136 that extends through the distal flange 134a of the adaptor 130.

As shown in FIG. 3, the adaptor 130 may include a cavity 132 that is configured to receive both the pressure transducer 140 and the base plate 142 that is attached or otherwise coupled to the pressure transducer 140.

The pressure transducer 140 may be in fluid communication with the fluid reservoir 112 of the syringe barrel 110 when the syringe assembly 100 is in a locked configuration. Stated differently, fluid from the fluid reservoir 112 of the syringe barrel 110 may pass through a side wall of the syringe barrel 110 and through the base plate 142 such that the pressure transducer 140 is in fluid communication with the fluid reservoir 112 defined by the syringe barrel 110. In other words, in some embodiments, fluid may pass through an aperture 116 (or a group of apertures) that extends through both a wall of the syringe barrel 110 and the base plate 142. In some embodiments, a cross-section of the aperture 116 has a radius that is less than or equal to 0.8 mm, 0.6 mm, and/or 0.4 mm in length. The geometry of the aperture 116 may minimize or otherwise reduce the entry of air bubbles into the aperture 116. For example, the size, shape, and/or position of the aperture 116 relative to other components may minimize or prevent the entrapment of air therein. In some embodiments, a seal (not shown) may be disposed between the base plate 142 and the syringe barrel 110, thereby providing an airtight seal between the base plate 142 and the syringe barrel 110. Additionally or alternatively, the base plate 142 may be bonded to the syringe barrel 110 via an adhesive.

The base plate 142 may be made from any suitable material (e.g., fluid impermeable material). For example, in some embodiments, the base plate 142 includes a ceramic board and a plurality of electrical conduits that extend from the transducer 140 to a plurality of electrical contacts 144, such as those depicted adjacent the proximal end of the base plate 142 in FIG. 3. When in operation, the pressure transducer 140 may convert pressure into an analog electrical signal. The signal may then be relayed to the electrical contacts 144 via the electrical conduits. When the syringe assembly 100 is in the locked configuration, the pressure transducer 140 and the base plate 142 may be disposed between the adaptor 130 and a lock 154.

The actuator 146 may be configured to power up the syringe assembly 100. Stated differently, the actuator 146 may be used to toggle the syringe assembly 100 between a disabled state and an enabled state. In other or further embodiments, the actuator 146 may be configured to communicate with the circuit board 170 and the display screen 190 such that manipulation of the actuator 146 causes the display screen 190 to transition between different visual displays. In the depicted embodiment, the practitioner may press upward on a button located on the underside of the lower portion of the housing 120b to manipulate the actuator 146.

The key 160 may include a hub 162, a plurality of arms 164, and an elongate shaft 166 that includes a tip 168. The elongate shaft 166 may extend from the hub 162 in a first direction, while each arm 164 extends from the hub 162 in a second direction that differs from the first direction. For example, the elongate shaft 166 may extend from the hub in a generally horizontal direction, while each arm 164 extends from the hub in generally an upward direction (e.g., toward a display screen 190 within the housing 120).

The key 160 may be configured to extend through an orifice in the housing 120 to displace a lock 154 and transition the syringe assembly 100 from a locked configuration to an unlocked configuration, as described in greater detail below.

The elastomeric connector 150 may be configured to electrically couple the pressure transducer 140 to a circuit board 170. Stated differently, the elastomeric connector 150 may establish an electrical connection with both the electrical contacts 144 of the base plate 142 and the circuit board 170. In some embodiments, the elastomeric connector 150 may include compressible material, such as silicone rubber. Such material may allow the elastomeric connector 150 to be compressed when squeezed by opposing forces provided by the base plate 142 and the circuit board 170.

In some embodiments, the elastomeric connector 150 includes a plurality of vertically oriented layers. The layers may be arranged in an alternating pattern, with conductive layers adjacent to non-conductive layers. An electrical signal that is relayed to the electrical contacts 144 of the base plate 142 from the pressure transducer 140 may be conveyed to the circuit board 170 via the one or more conductive layers of the elastomeric connector 150. In this manner, a solderless electrical connection between the pressure transducer 140 and the circuit board 170 may be established.

The circuit board 170 may include circuitry and a plurality of holes 172. The circuitry may include logic to facilitate the conversion of a signal from the pressure transducer into a readout that is representative of the pressure within the fluid reservoir 112 of the syringe barrel 110.

The power source(s) 180 (e.g., a battery) may be configured to convert stored chemical energy into electrical energy to power one or more components of the syringe assembly 100.

The display screen 190 may be configured for electrical communication with the circuit board 170 and the pressure transducer 140. For example, a signal from the pressure transducer 140 that is representative of the pressure within the fluid reservoir 112 of the syringe barrel 110 may be relayed to the electrical contacts 144 of the base plate 142 via one or more electrical conduits. The signal may then be further relayed from the electrical contacts 144 of the base plate 142 to the circuit board 170 via a solderless connection (e.g., via the elastomeric connector 150). After the signal has been processed by the circuit board 170, the circuit board 170 may send or relay a signal to a display screen 190. The display screen 190 may then provide a visible readout that is representative of the pressure within the fluid reservoir 112 of the syringe barrel 110.

The upper portion of the housing 120a may be configured to couple to the lower portion of the housing 120b to enclose the display screen 190, the circuit board 170, and/or the power source(s) 180.

Figure 4:
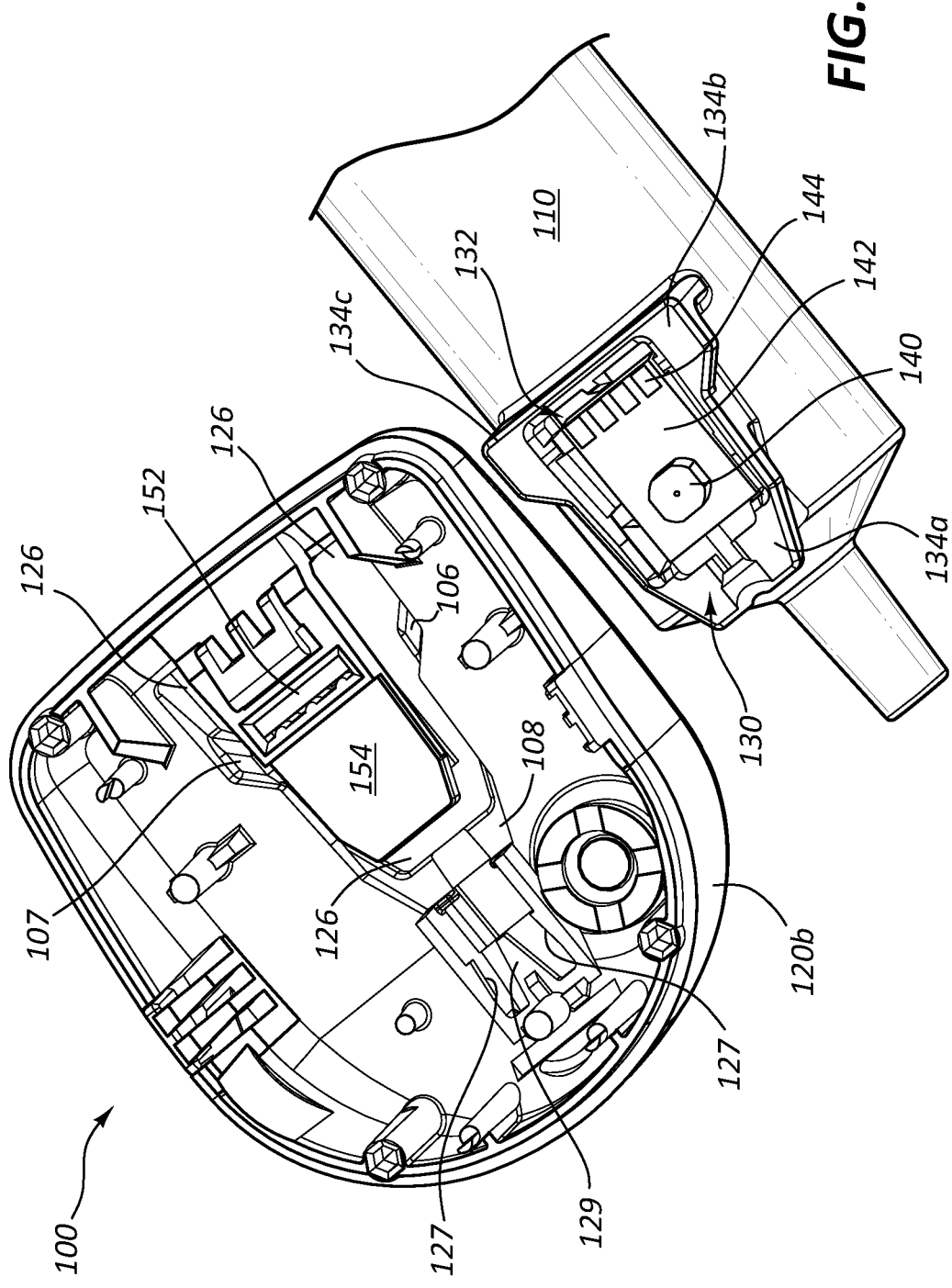
FIG. 4 is a perspective view of a portion of the syringe assembly of FIG. 1, with a syringe barrel uncoupled from a lower portion of a housing.
Figure 5:
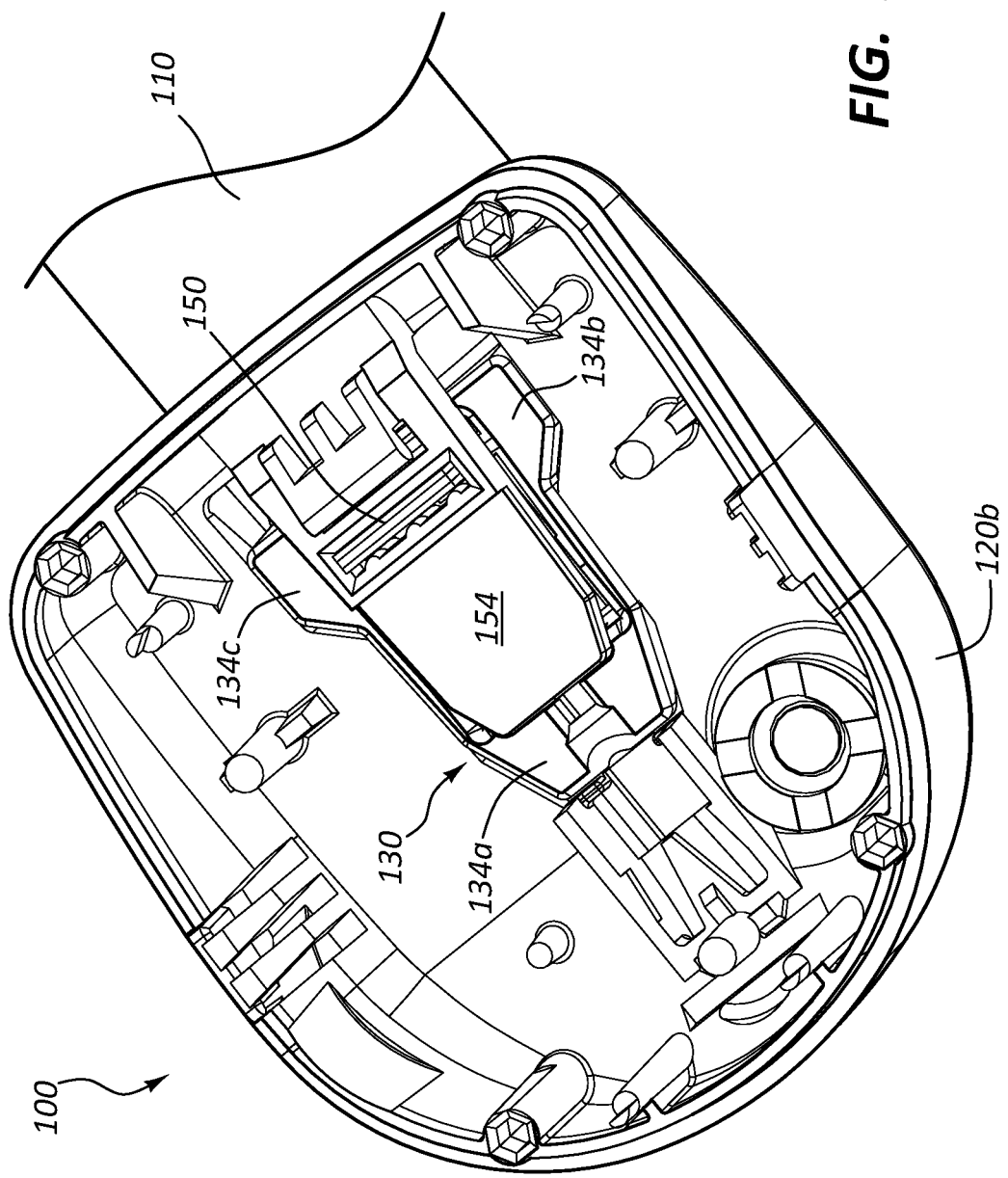
FIG. 5 is a perspective view of the portion of the syringe assembly depicted in FIG. 4, with the syringe barrel coupled to the lower portion of the housing.

FIG. 4 provides a perspective view of a portion of the syringe assembly 100, with the syringe barrel 110 uncoupled from a lower portion of the housing 120b. FIG. 5 provides a perspective view of the portion of the syringe assembly 100 depicted in FIG. 4, with the syringe barrel 110 coupled to the lower portion of the housing 120b via an adaptor 130. In both FIGS. 4 and 5, the upper portion of the housing, the display screen, the circuit board, and power sources have been removed for clarity.

With reference to FIGS. 4 and 5, the lower portion of the housing 120b may be configured to couple to the elongate syringe barrel 110. For instance, with the pressure transducer 140 and the base plate 142 disposed within the cavity 132 of the adaptor 130, the adaptor 130 may be inserted through an opening 126 in the lower portion of the housing 120b and subsequently attached or otherwise coupled to the lower portion of the housing 120b. When fully engaged, the first proximal flange 134b may rest upon a first surface of the lower portion of the housing 120b. The second proximal flange 134b may rest upon a second surface of the lower portion of the housing 120b. And the distal flange 134a may rest on a third surface of the lower portion of the housing 120b.

In the depicted embodiment, a lock 154 is attached or otherwise coupled to the lower portion of the housing 120b. For example, in some embodiments, the lock 154 is integrally formed with the lower portion of the housing 120b. The lock 154 may include a slot 152 (see FIG. 4) that is configured to receive an elastomeric connector 150 (see FIG. 5). In other words, the elastomeric connector 150 may extend through the lock 154 to electrically couple the pressure transducer 140 to the circuit board 170. The locking mechanism for the lock 154 is discussed in greater detail below in connection with FIGS. 6-14.

Figure 6:
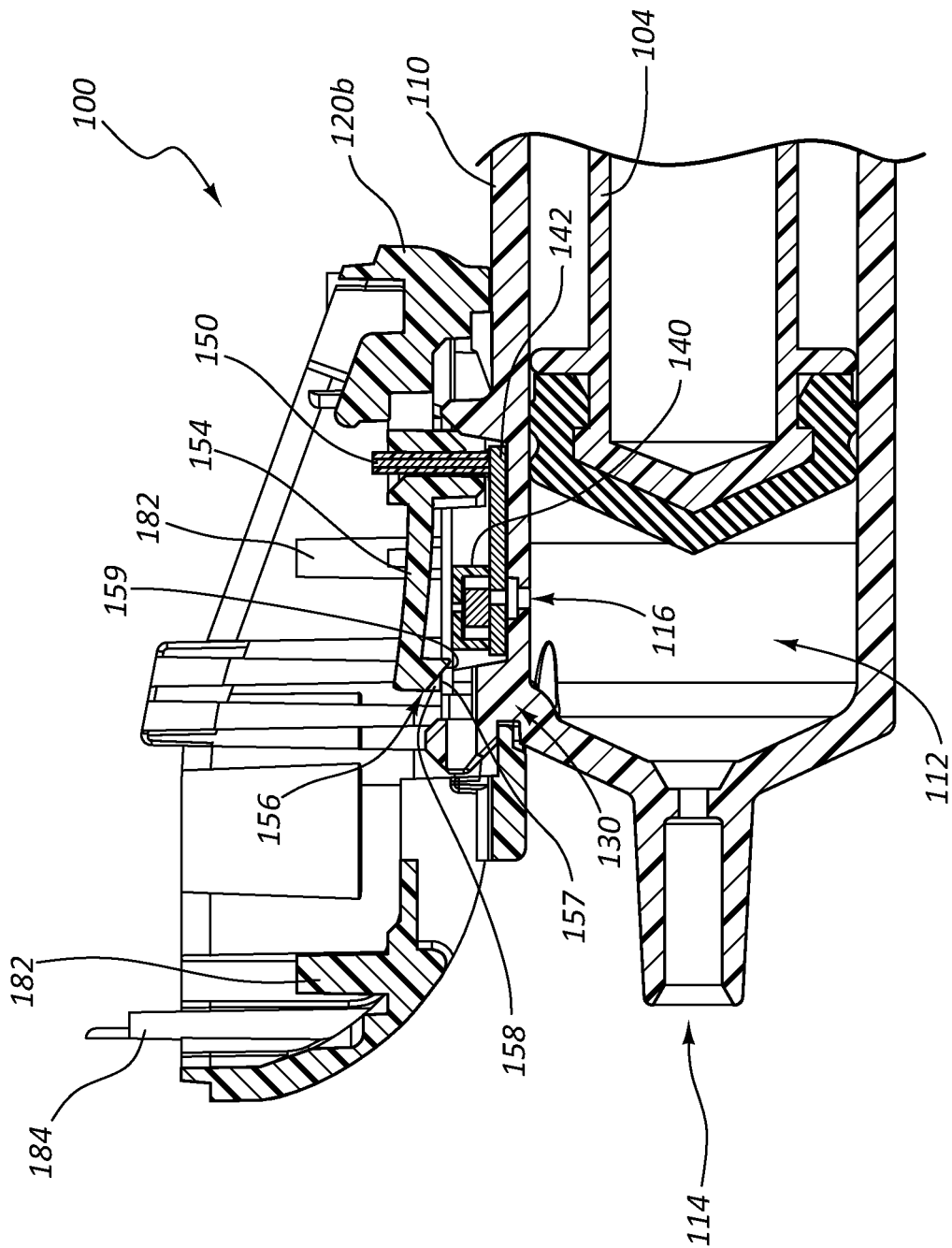
FIG. 6 is a cross-sectional side view of a portion of the syringe assembly of FIG. 1 in an unlocked configuration.
Figure 7:
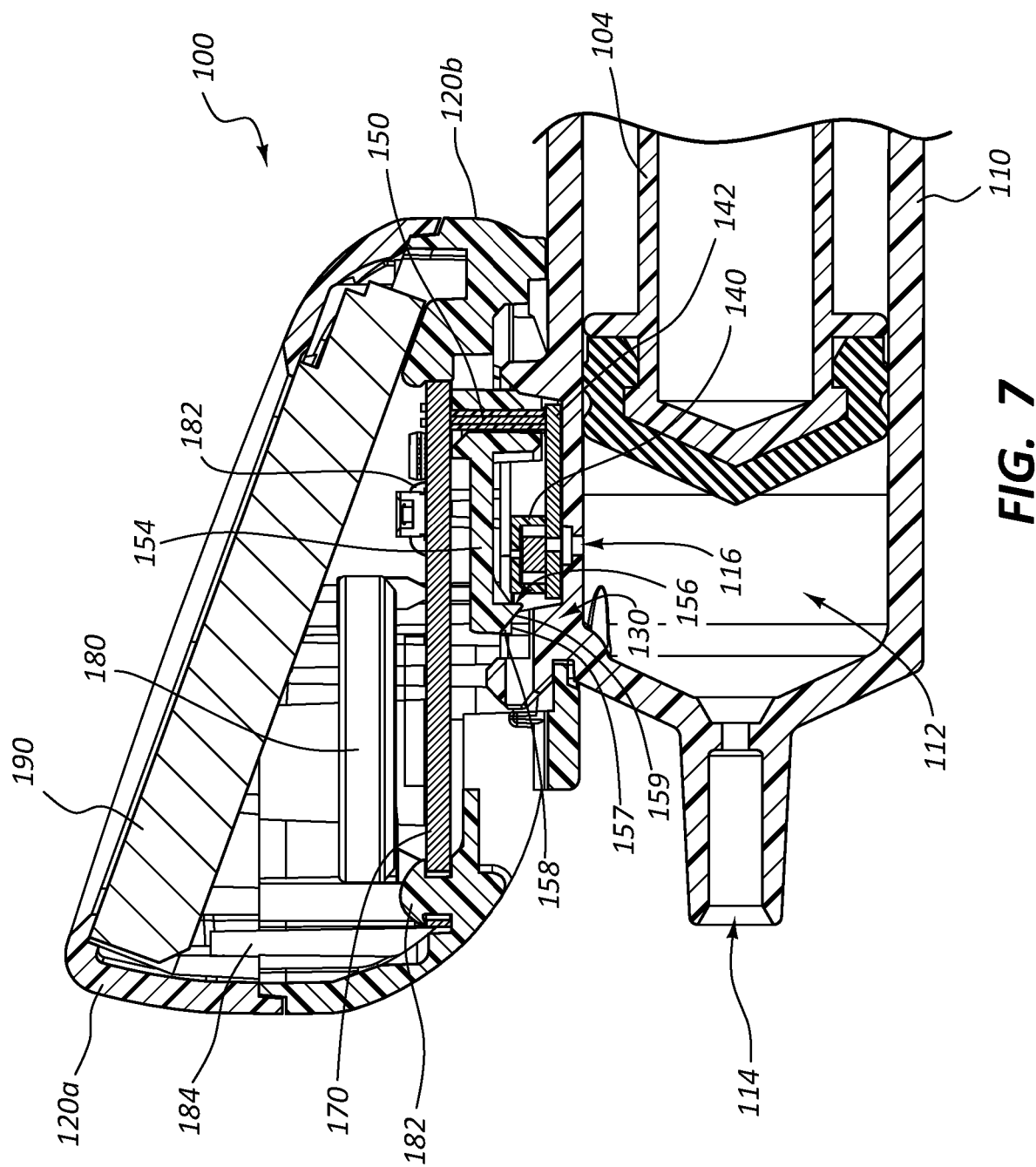
FIG. 7 is a cross-sectional view of a portion of the syringe assembly of FIG. 1, with the syringe assembly in a locked configuration.
Figure 8:
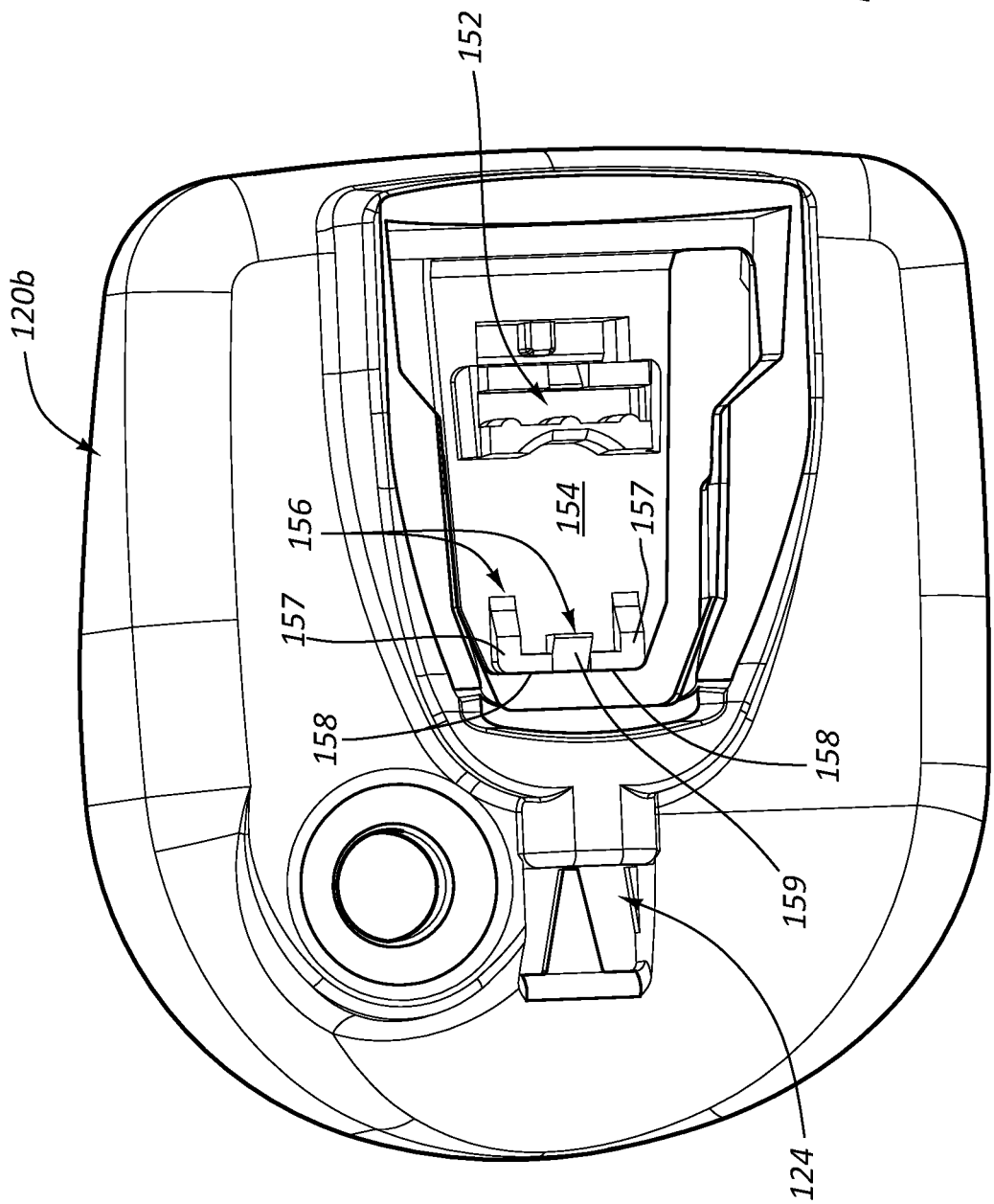
FIG. 8 is a perspective view of a lower portion of the housing of the syringe assembly of FIG. 1.

FIGS. 6 and 7 provide cross-sectional views of portions of the syringe assembly 100, while FIG. 8 provides a perspective view of the underside of the lower portion of the housing 120b. More particularly, FIG. 6 provides a cross-sectional view of a portion of the syringe assembly 100 in an unlocked and partially assembled configuration, while FIG. 7 depicts a distal portion of the syringe assembly 100 in a locked and fully assembled configuration.

With reference to FIG. 6, the adaptor 130 may exert an upward force on a lock 154 that is coupled to the lower portion of the housing 120b as the adaptor 130 is inserted through the opening 126 of the lower portion of the housing 120b as described above in connection with FIGS. 4 and 5. For example, as depicted in FIG. 6, as the adaptor 130 is inserted into the lower portion of the housing 120b, a distal portion of the lock 154 may be deflected in an upward direction.

As shown in FIGS. 6-8, the lock 154 may include a first (e.g., proximal) portion for coupling to the lower portion of the housing 120b, and a second (e.g., distal) portion that is configured to deflect upward as the adaptor 130 is inserted into the opening of the lower portion of the housing 120b. The second portion of the lock 154 may also include a downward protrusion 156. In the depicted embodiment, the downward protrusion 156 includes one or more bottom surfaces 157, one or more locking surfaces 158, and an angled surface 159.

As the adaptor 130 is inserted into the lower portion of the housing 120b, the bottom surfaces 157 of the downward protrusion 156 may contact the adaptor 130, thereby displacing the lock 154 in an upward direction as shown in FIG. 6. Once the adaptor 130 is fully inserted into the lower portion of the housing 120b, the lock 154 may return to its original position as shown in FIG. 7. With the adaptor 130 fully inserted, the locking surfaces 158 of the downward protrusion 156 may abut against the adaptor 130, thereby preventing movement of the lower portion of the housing 120b relative to the adaptor 130. In this manner, the adaptor 130 may be locked in place relative to the lower portion of the housing 120b via a lock 154 that is coupled to the lower portion of the housing 120b.

Some components or elements of the syringe assembly 100 labeled in FIGS. 6, 7 and/or 8 (e.g., the upper portion of the housing 120a, the display screen 190, the power source 180, the elastomeric connector 150, the pressure transducer 140, the base plate 142, the aperture 116, the distal port 114, the fluid reservoir 112, the syringe barrel 110, and the plunger 104) are described in connection with other figures. Other or further components of the syringe assembly 100 are structurally analogous to and/or operate in like fashion to components described in U.S. Provisional Pat. Appl. No. 62/188,997, titled "HOUSING FOR USE WITH INFLATION DEVICES AND RELATED METHODS," which is hereby incorporated by reference in its entirety. For example, the circuit board 170 may be coupled to the housing via one or more heat pins 182 in a manner analogous to that described in U.S. Provisional Pat. Appl. No. 62/188,997. Similarly, the display screen 190 may rest upon one or more resilient pins 184 in a manner analogous to that described in U.S. Provisional Pat. Appl. No. 62/188,997.

Figure 9:
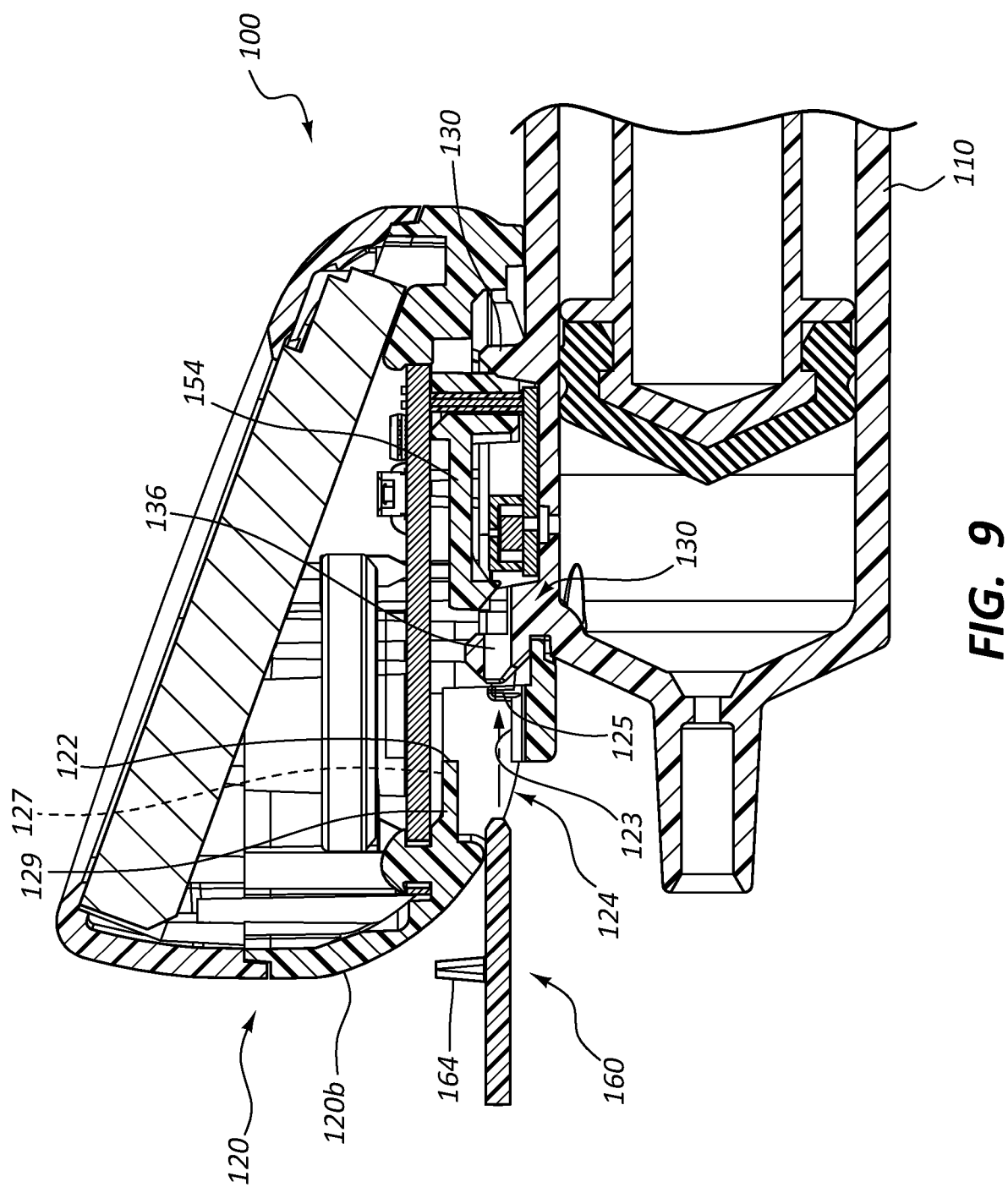
FIG. 9 is a cross-sectional side view of a portion of the syringe assembly of FIG. 1, showing partial insertion of a key into the housing.
Figure 10:
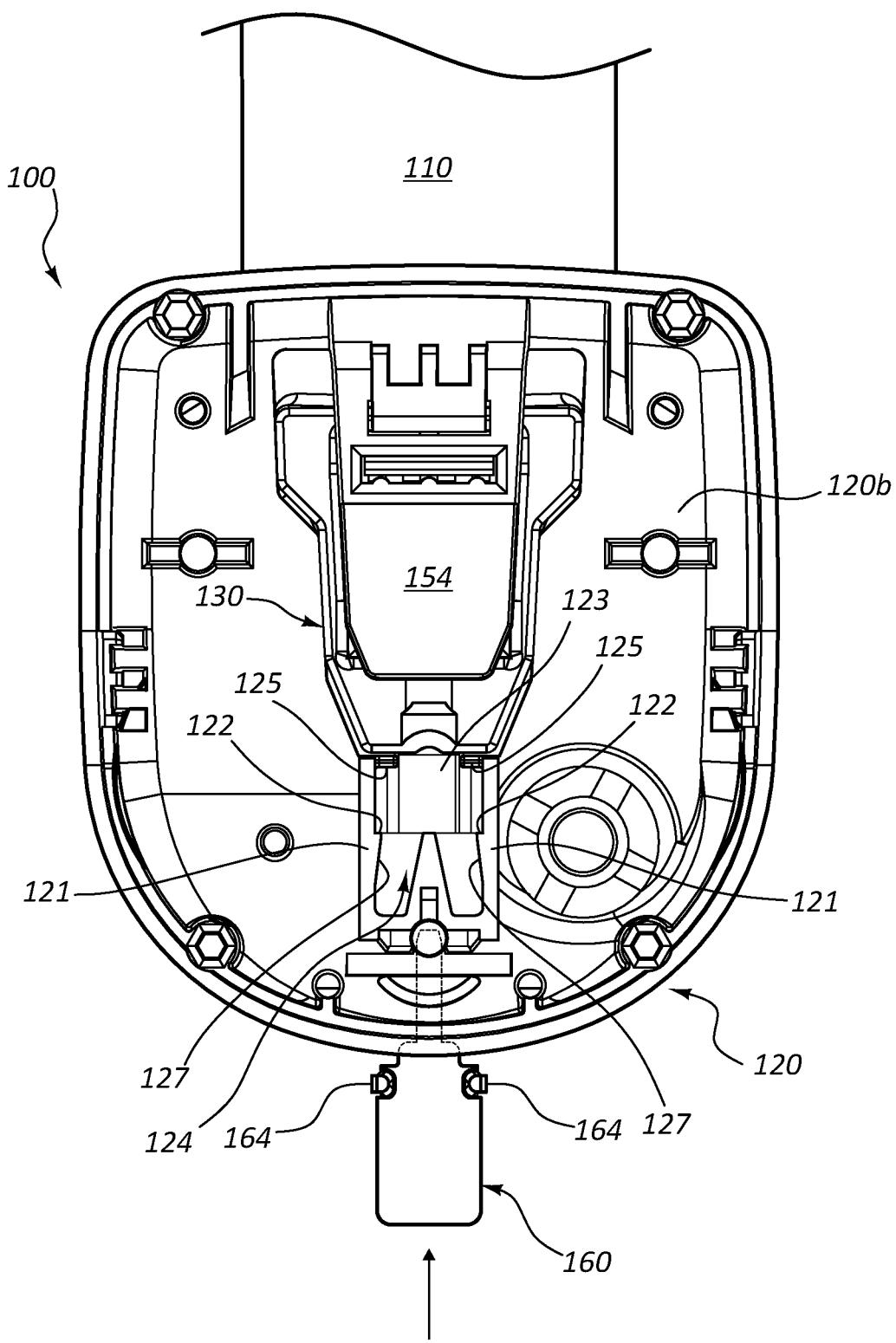
FIG. 10 is a top view of a portion of the syringe assembly of FIG. 1, with the key partially inserted into the housing as shown in FIG. 9.
Figure 11:
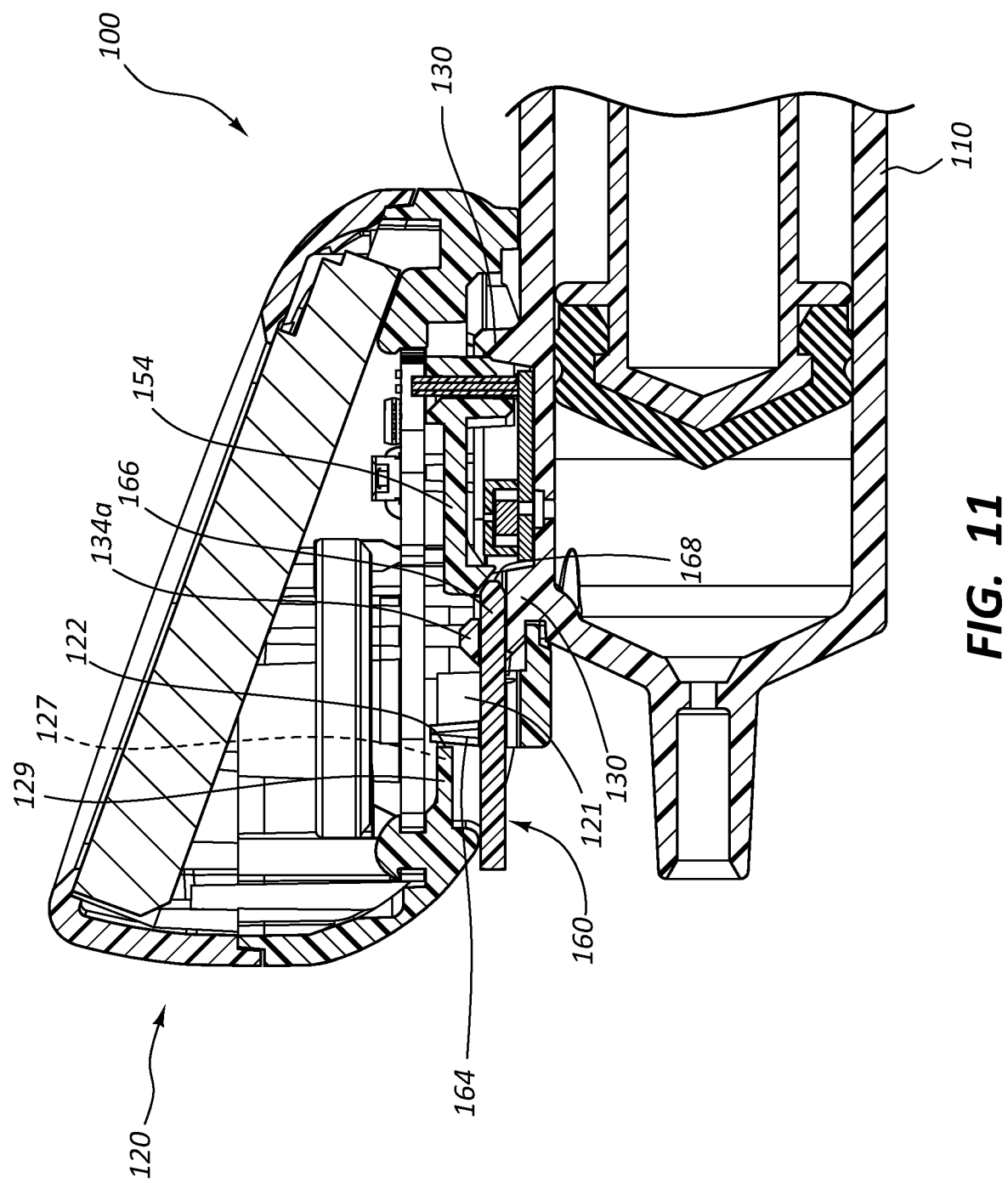
FIG. 11 is a cross-sectional side view of a portion of the syringe assembly of FIG. 1, wherein the arms of the key are positioned immediately proximal of catches of the housing.
Figure 12:
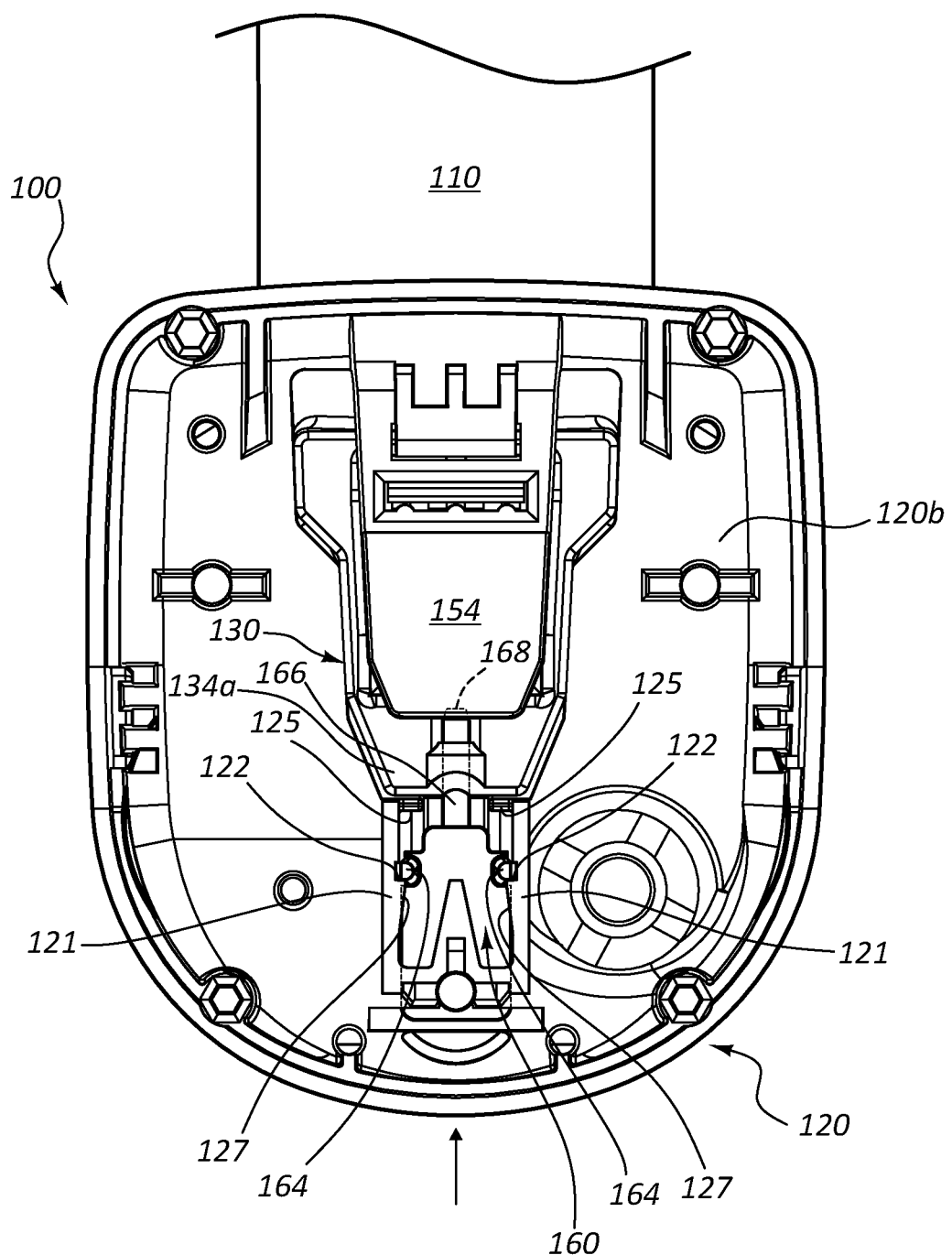
FIG. 12 is a top view of a portion of the syringe assembly of FIG. 1, with the key positioned as shown in FIG. 11.
Figure 13:
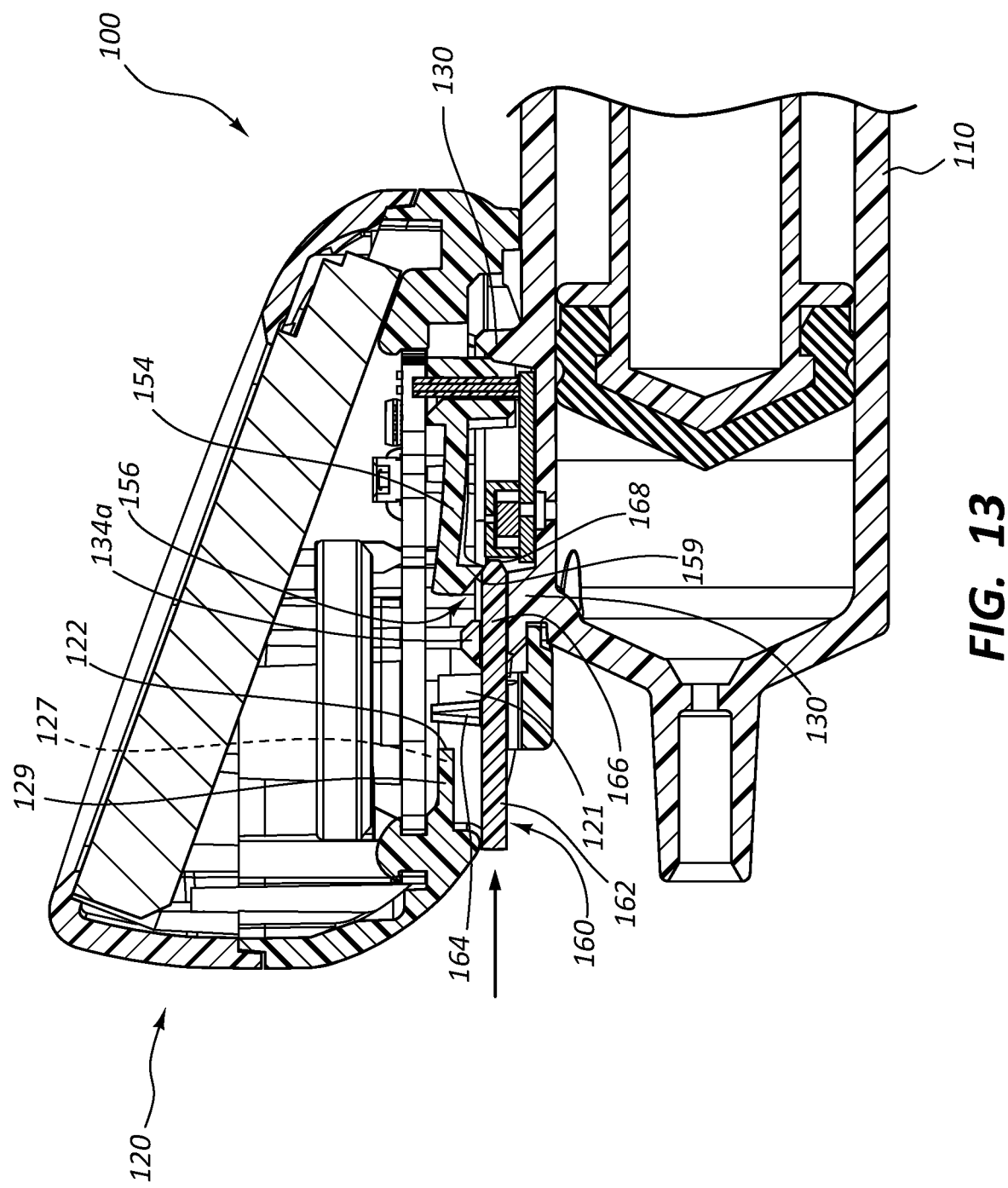
FIG. 13 is a cross-sectional side view of a portion of the syringe assembly of FIG. 1 in which a tip of the key contacts and displaces the lock.
Figure 14:
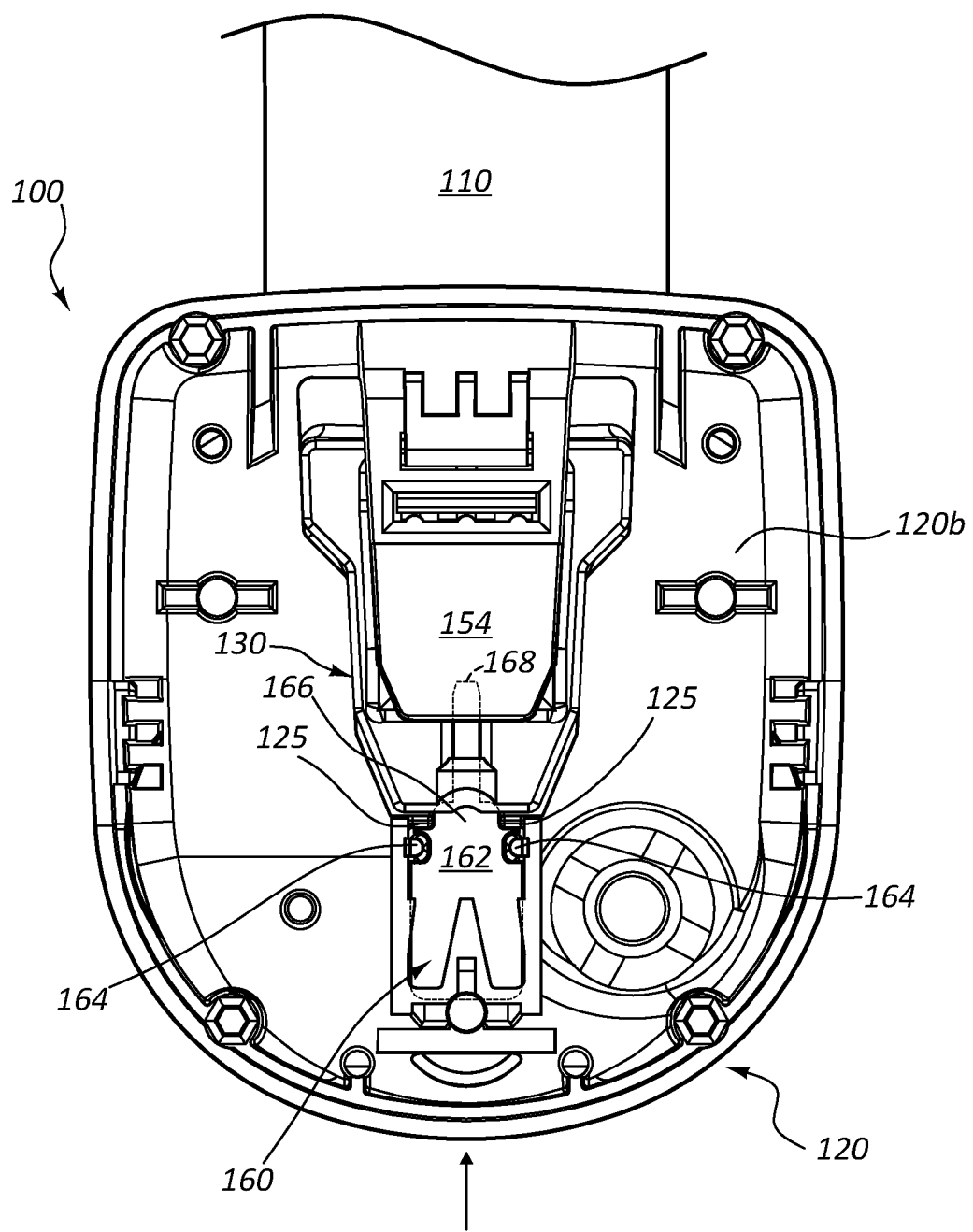
FIG. 14 is a top view of a portion of the syringe assembly of FIG. 1 with the key positioned as shown in FIG. 13.

FIGS. 9-14 provide various views of portions of the syringe assembly 100 as the syringe assembly 100 transitions from a locked configuration in which the lock 154 prevents movement of the adaptor 130 relative to the housing 120 to an unlocked configuration in which the adaptor 130 is free to move relative to the housing 120. More particularly, FIGS. 9 and 10 provide alternative views of a portion of the syringe assembly 100 in a locked configuration as a key 160 is initially inserted into the housing 120. FIGS. 11 and 12 provide alternative views of the same portion of the syringe assembly 100 in a locked configuration, with the key 160 positioned such that the arms 164 of the key 160 are disposed immediately proximal of one or more catches 122 of the housing 120. FIGS. 13 and 14 provide alternative views of the same portion of the syringe assembly 100, in which the key 160 engages with the lock 154 to transition the syringe assembly 100 to an unlocked configuration. FIGS. 9, 11, and 13 provide cross-sectional side views of a portion of the syringe assembly 100, while FIGS. 10, 12, and 14 provide top views of the same portion of the syringe assembly 100 with the upper portion of the housing, the display screen, the power source(s), and the circuit board removed for clarity.

More particularly, with reference to FIGS. 9 and 10, once the syringe assembly 100 is in the locked configuration described above in connection with FIG. 7, a key 160 may inserted through an orifice 124 in the lower portion of the housing 120b to detach the housing 120 from the remainder of the syringe assembly 100. Stated differently, after the syringe assembly 100 has been used in a medical procedure, the housing 120 may be uncoupled from the adaptor 130, thereby transitioning the syringe assembly from a locked configuration to an unlocked configuration.

As shown in FIGS. 9 and 10, the lower portion of the housing 120b may include a plurality of side walls 121, a support surface 123, one or more barrier walls 125, one or more angled surfaces 127, a projection 129, and one or more catches 122. The plurality of side walls 121 may extend generally parallel to the longitudinal axis of the syringe assembly 100. In the depicted embodiment, the side walls 121 are vertically oriented to partially define the orifice 124. The one or more barrier walls 125 may be coupled to and disposed adjacent the proximal ends of the side walls 121. Each barrier wall 125 may extend inward from a side wall 121 toward the longitudinal axis of the syringe assembly 100. The side walls 121 may have a height that is greater than the height of the barrier walls 125.

In the depicted embodiment, each angled surface 127 extends longitudinally from adjacent the distal end of a side wall 121 to a position distal of the proximal end of the side wall 121. The angled surface 127 also extends inward from the side wall 121 such that a proximal portion of the angled surface 127 extends further inward (e.g., toward the longitudinal axis of the syringe assembly 100) than a distal portion of the angled surface 127. In the depicted embodiment, each angled surface 127 is disposed adjacent the top of the side wall 121, but does not extend to the bottom of the side wall 121. Stated differently, the angled surfaces 127 may extend inward from a side wall 121 only along a portion of the height of the side wall 121. For instance, in the depicted embodiment, the angled surfaces 127 have a height that is substantially identical to the height of the projection 129 (see FIG. 4). The proximal ends of the angled surfaces 127 and the corresponding side walls 121 may cooperate to form one or more catches 122 that are configured to prevent complete withdrawal of the key 160 from the housing 120 as described below.

As the key 160 is inserted through the orifice 124 of the housing 120 as shown in FIGS. 9 and 10, the key 160 may slide along the support surface 123 of the housing 120. During such insertion, each arm 164 of the key 160 may be deflected inward due to interaction of the arm 164 with an angled surface 127 until the arm 164 is disposed proximal of the catches 122 as shown in FIGS. 11 and 12. As the arms 164 are displaced past the catches 122, the arms 164 may be biased to snap outward toward the side walls 121, thereby preventing complete withdrawal of the key 160 from the housing 120 due to interaction of the arms 164 with the proximal surfaces of the catches 122.

When the key 160 is positioned as shown in FIGS. 11 and 12 (i.e., with the arms 164 disposed immediately proximal of the catches 122), the elongate shaft 166 of the key 160 may extend through a channel 136 (see FIG. 9) of the adaptor 130. Stated differently, the tip 168 of the elongate shaft 166 may be disposed proximal of the distal flange 134a of the adaptor 130 as shown in FIGS. 11 and 12. When positioned as shown in FIGS. 11 and 12, the tip 168 of the elongate shaft 166 does not push against the lock 154 to transition the syringe assembly 100 from the locked configuration to the unlocked configuration.

In some circumstances, the syringe assembly 100 may be delivered to a practitioner and/or used for a medical procedure with the key 160 positioned as shown in FIGS. 11 and 12. Stated differently, with the key 160 disposed as shown in FIGS. 11 and 12, the syringe assembly 100 may be in an operational configuration that permits use of the syringe assembly 100 in a medical procedure.

To transition the syringe assembly 100 from the locked configuration depicted in FIGS. 11 and 12 to an unlocked configuration in which the adaptor 130 is free to move relative to the housing 120 as shown in FIGS. 13 and 14, the key 160 may be pushed in a proximal direction (e.g., until stopped by the barrier walls 125), thereby causing the tip 168 of the key 160 to contact and displace the lock 154. For example, as the key 160 is displaced in a proximal direction, the tip 168 of the key 160 may contact an angled surface 127 of the lock 154, thereby lifting the distal end of the lock 154. By lifting the distal end of the lock 154 in this manner, the adaptor 130 may be moved in a proximal direction relative to the housing 120 without interference from the downward protrusion 156 of the lock 154, thereby permitting separation of the adaptor 130 (and the syringe barrel 110 to which it is coupled) from the housing 120. In some embodiments, insertion of the key 160 may be limited by the barrier walls 125, which contact the hub 162 of the key 160 once the key 160 is properly positioned to displace the lock 154 and permit separation of the adaptor 130 from the housing 120.

As is apparent from the foregoing disclosure, a practitioner or other individual may carry out one or more methods to separate components of a pressure-sensing inflation device (e.g., the syringe assembly 100) once the inflation device has been used in a medical procedure. For example, in some methods, an individual may obtain an inflation device, such as the syringe assembly 100 described above, with the inflation device in a locked configuration. The individual may then move a key 160 toward a lock 154 of the inflation device, thereby causing displacement of the lock 154. Such displacement may transition the inflation device from a locked configuration to an unlocked configuration. Once the lock 154 has been displaced, the housing 120 of the inflation device may be separated from the syringe barrel 110.

In some embodiments, the step of moving the key 160 toward the lock 154 may include at least partially inserting the key 160 into the housing 120. In some embodiments, the step of moving the key 160 toward the lock 154 may include pushing directly onto the hub 162 of the key 160.

In some embodiments, one or more of the circuit board 170, the display screen 190 and the housing 120 may be sent to a refurbisher after the syringe barrel 110 has been separated from the housing 120. In some embodiments, the syringe barrel 110 may be discarded once the syringe barrel 110 has been separated from the housing 120. In some embodiments, one or more of the circuit board 170 and the display screen 190 may be removed from the housing 120 after the housing 120 has been separated from the syringe barrel 110.

Figure 15:
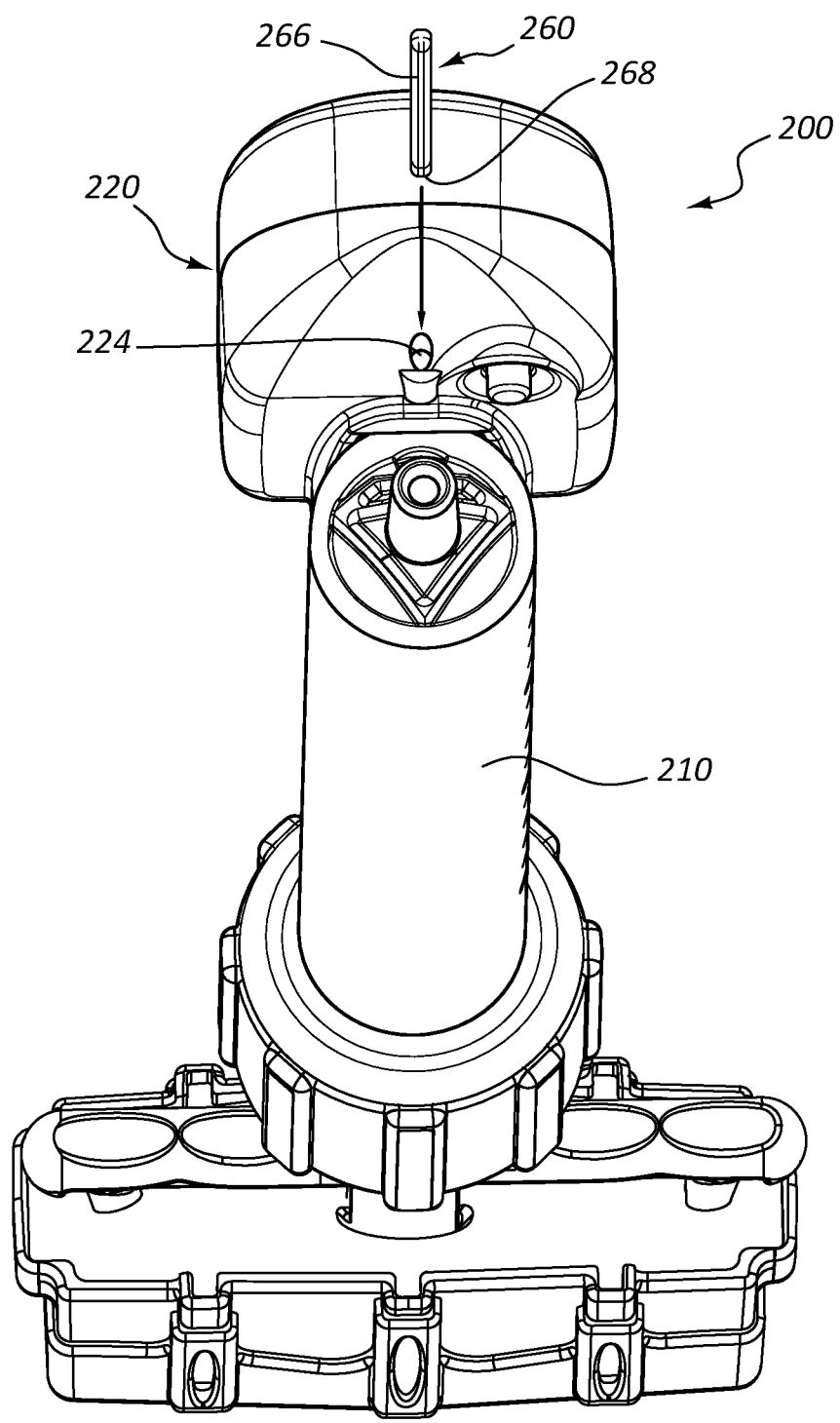
FIG. 15 is a perspective view of a syringe assembly, according to another embodiment.
Figure 16:
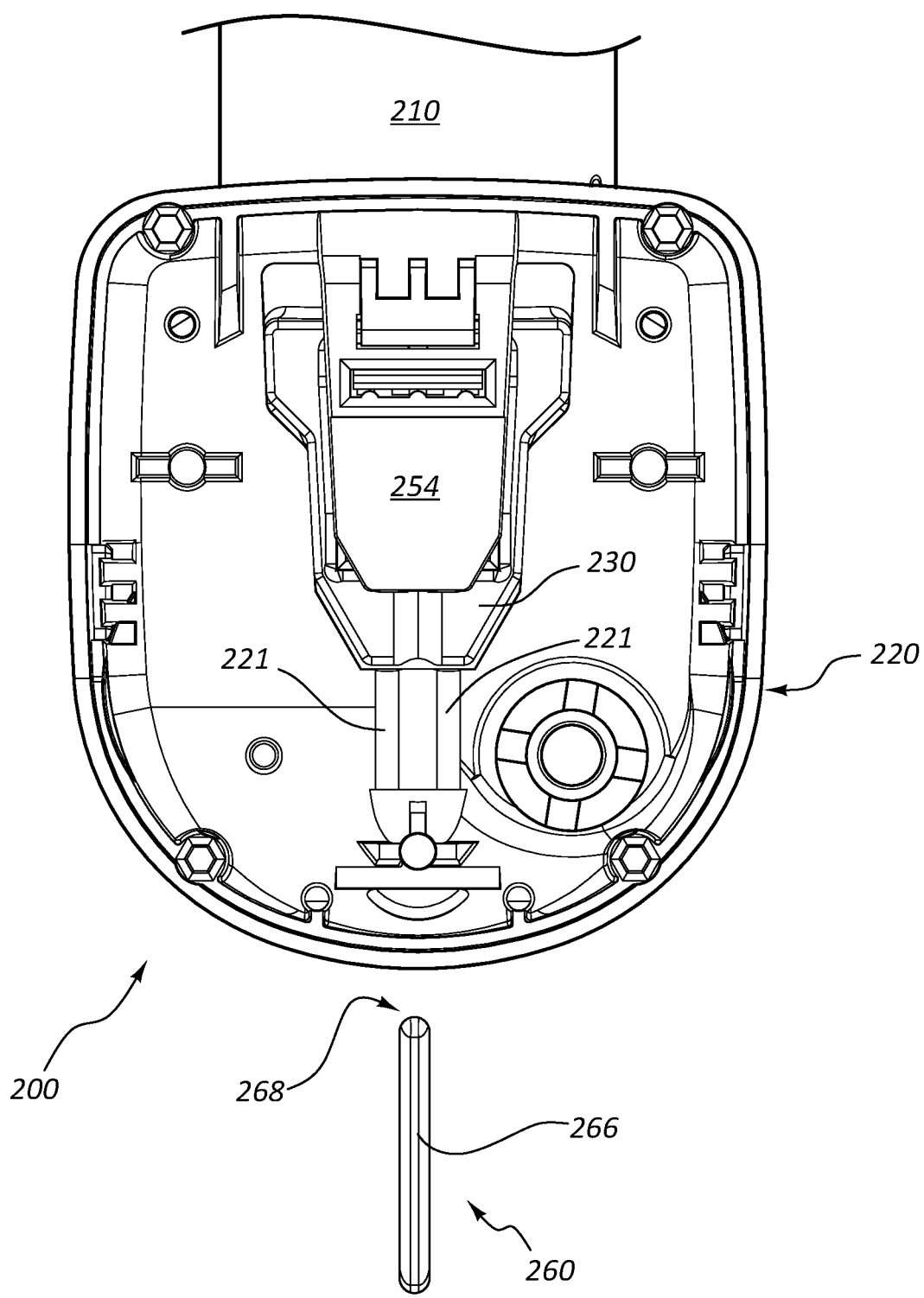
FIG. 16 is a top view of a portion of the housing of the syringe assembly of FIG. 15.
Figure 17:
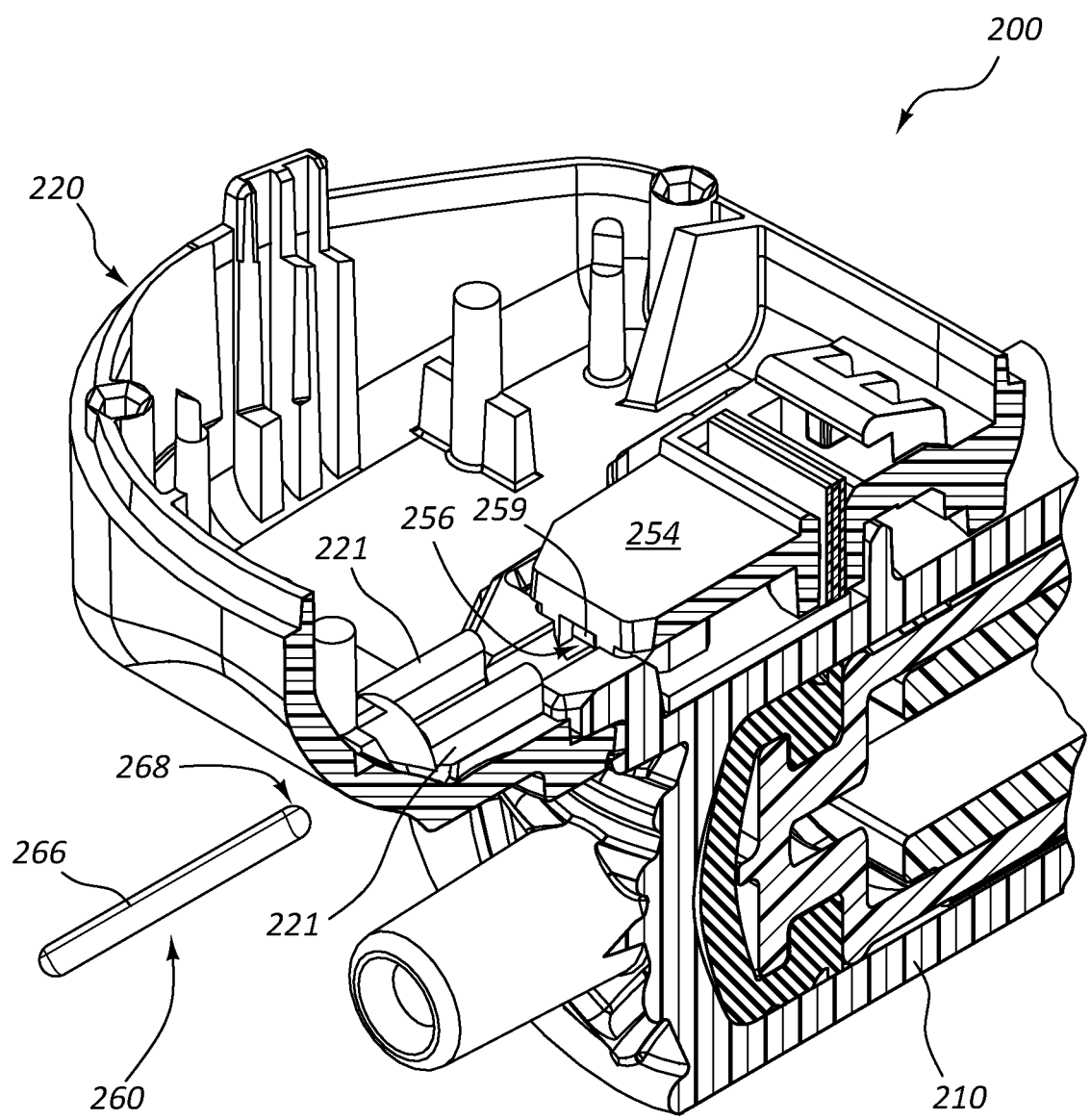
FIG. 17 is a perspective cross-sectional view of a portion of the syringe assembly of FIG. 15.

FIGS. 15-17 depict an embodiment of a syringe assembly 200 that resembles the syringe assembly 100 described above in certain respects. Accordingly, like features are designated with like reference numerals, with the leading digits incremented to "2." For example, the embodiment depicted in FIGS. 15-17 includes a syringe barrel 210 that may, in some respects, resemble the syringe barrel 110 of FIGS. 1-14. Relevant disclosure set forth above regarding similarly identified features thus may not be repeated hereafter. Moreover, specific features of syringe assemblies and related components shown in FIGS. 1-14 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the syringe assembly 200 and related components depicted in FIGS. 15-17. Any suitable combination of the features, and variations of the same, described with respect to the syringe assembly 100 and related components illustrated in FIGS. 1-14 can be employed with the syringe assembly 200 and related components of FIGS. 15-17, and vice versa. This pattern of disclosure applies equally to further embodiments depicted in subsequent figures and described hereafter, wherein the leading digits may be further incremented.

FIG. 15 provides a perspective view of the syringe assembly 200. FIG. 16 provides a top view of a distal portion of the syringe assembly 200. FIG. 17 provides a cross-sectional perspective view of a distal portion of the syringe assembly 200. In FIGS. 16 and 17, the upper portion of the housing, the display screen, the circuit board, and power sources have been removed for clarity.

The syringe assembly 200 shown in FIGS. 15-17 is generally analogous to the syringe assembly 100, but differs from the syringe assembly 100 in that the lower portion of the housing 220 is designed to interact with a key 260 that can be withdrawn from the housing 220 once the key 260 has transitioned the syringe assembly 200 from a locked configuration to an unlocked configuration.

More specifically, in the depicted embodiment, the syringe assembly 200 includes a key 260 that comprises or consists essentially of an elongate shaft 266. To uncouple the housing 220 from the syringe barrel 210, the elongate shaft 266 of the key 260 may be inserted through an orifice 224 in the housing 220. In the depicted embodiment, the orifice 224 is sized just larger than the diameter of the elongate shaft 266 of the key 260, thereby allowing insertion of the elongate shaft 266 into the orifice 224 while minimizing the likelihood of contaminant entry. As the key 260 is inserted into the housing 220, the key 260 may extend through a channel that is at least partially defined by a plurality of the side walls 221. When fully inserted, the distal tip 268 of the key 260 may contact an angled surface 259 of the downward protrusion 256 of the lock 254, thereby displacing a distal portion of the lock 254 in an upward direction. Such upward displacement of the distal portion of the lock 254 may transition the syringe assembly 200 from a locked configuration to an unlocked configuration, thereby allowing separation of the housing 220 from the adaptor 230 and the syringe barrel 210. Once the lock 254 has been displaced by the key 260, the key 260 may be completely withdrawn from the housing 200. Stated differently, some embodiments may lack angled surfaces, catches, or other features that are analogous to the angled surfaces 127, catches 122, and other features shown in FIGS. 1-14 for preventing complete withdrawal of the key 260 from the housing 220.

Figure 18:
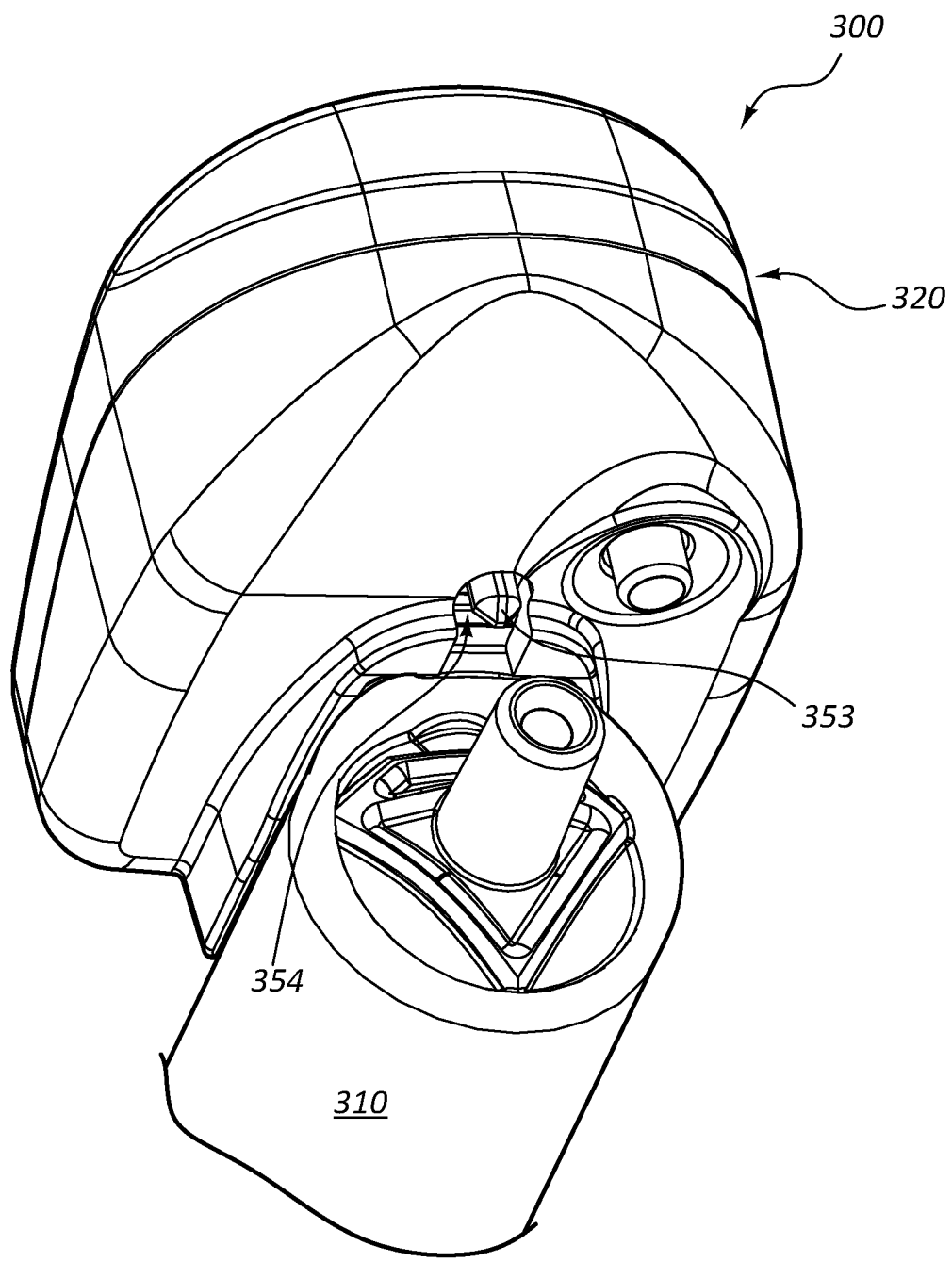
FIG. 18 is a perspective view of a distal portion of a syringe assembly, according to another embodiment.
Figure 19:
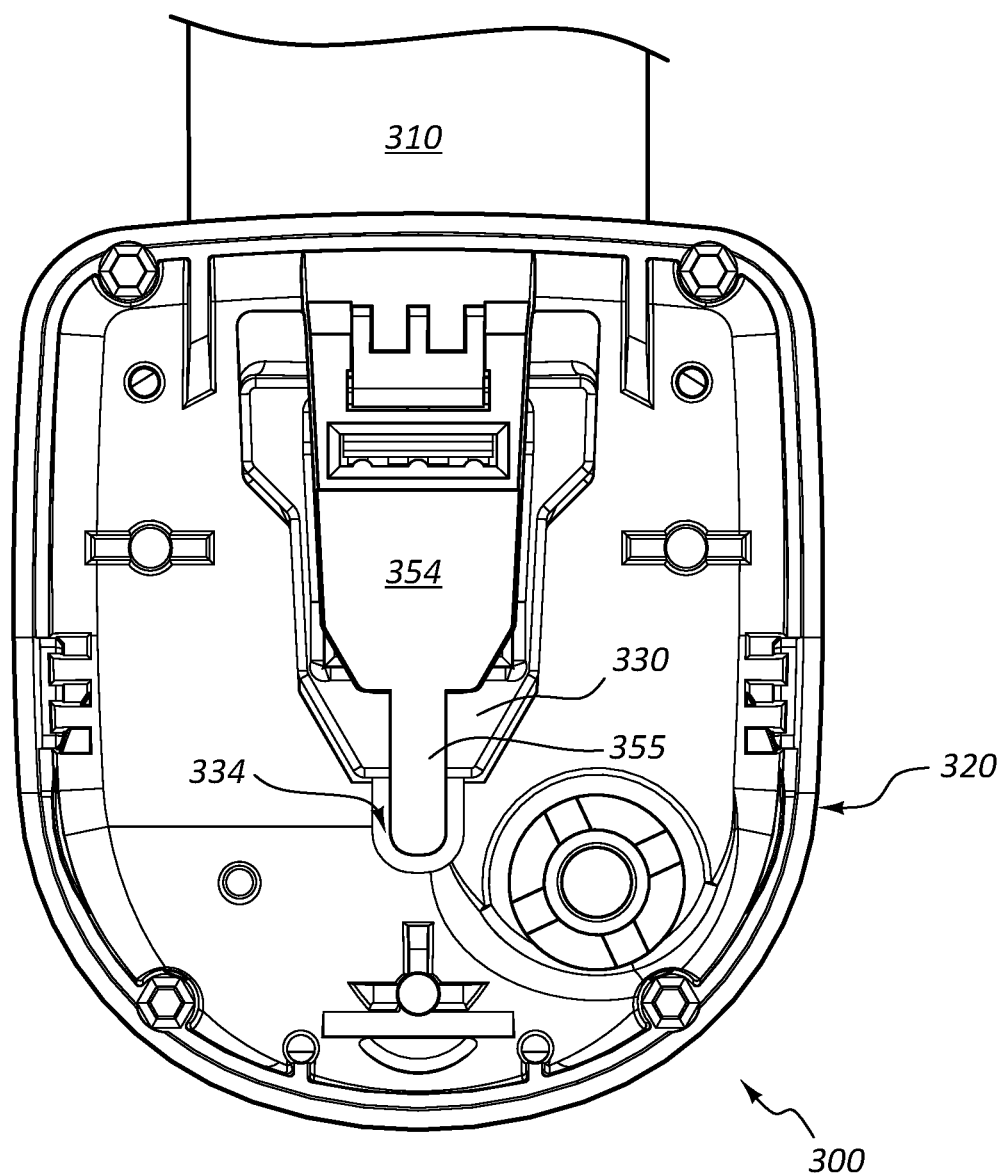
FIG. 19 is top view of a portion of the syringe assembly of FIG. 18.
Figure 20:
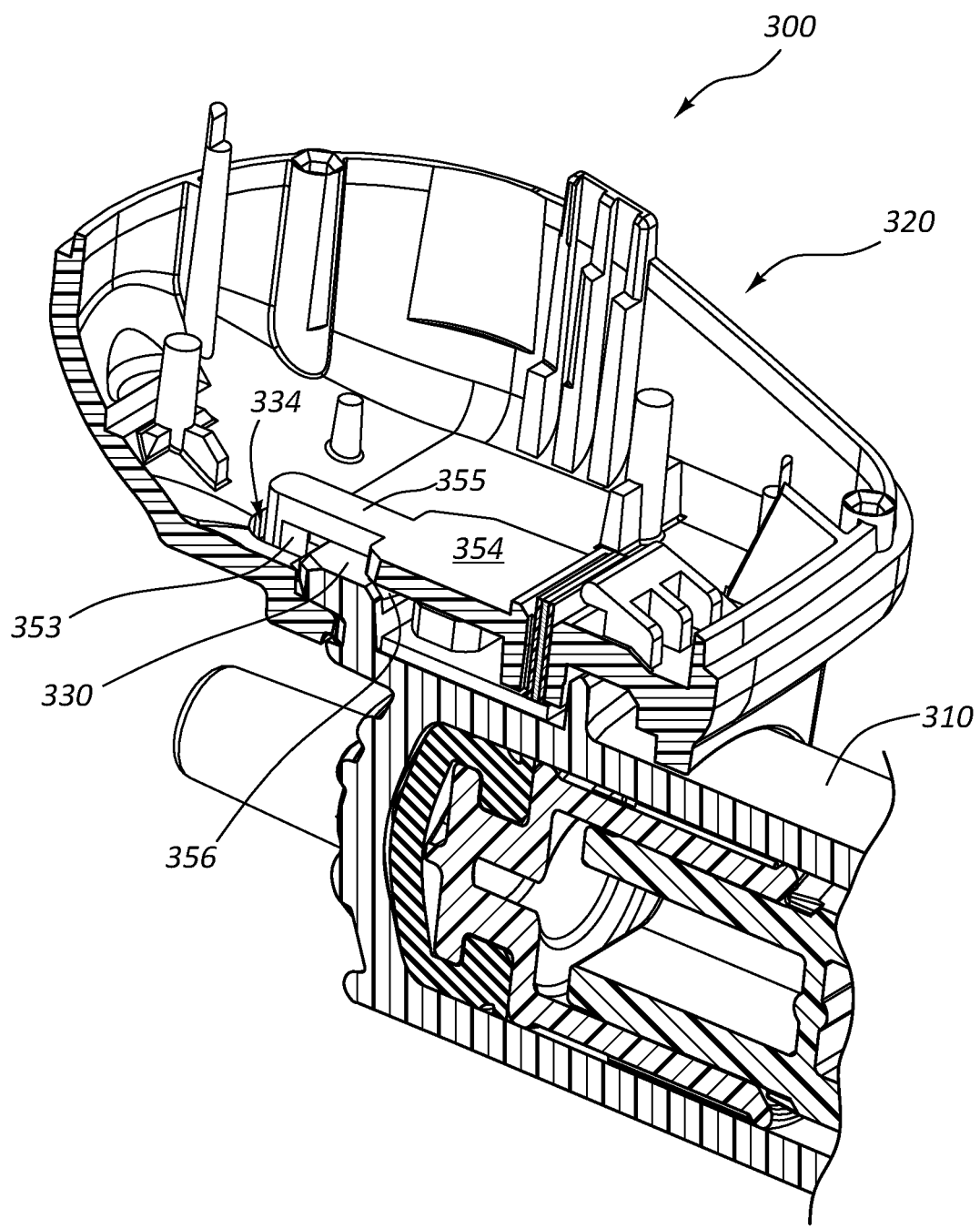
FIG. 20 is a perspective cross-sectional view of a portion of the syringe assembly of FIG. 18.

FIGS. 18-20 depict a syringe assembly 300, according to another embodiment. More particularly, FIG. 18 provides a perspective view of a distal portion of the syringe assembly 300. FIG. 19 provides a top view of a distal portion of the syringe assembly 300. And FIG. 20 provides a cross-sectional side view of a distal portion of the syringe assembly 300.

As depicted in FIGS. 18-20, the syringe assembly 300 generally resembles the syringe assemblies 100, 200 referenced above. However, the syringe assembly 300 provides a locking/unlocking mechanism that differs somewhat from the mechanisms discussed above.

More specifically, the embodiment depicted in FIGS. 18-20 includes a lock 354. The lock 354 includes a proximal portion that generally resembles the locks 154, 254 described above. For instance, the lock 354 may include a downward protrusion 356 that is configured to interact with the adaptor 330 to prevent movement of the syringe barrel 310 relative to the housing 320. The lock 354 further includes an extension arm 355 that extends distally from the remainder of the lock 354. The extension arm 355 is sized to extend beyond the adaptor 330 when the syringe assembly 300 is in a locked configuration.

The lock 354 may also include an actuator arm 353 that is disposed adjacent the distal end of the extension arm 355. The actuator arm 353 may extend downward from the extension arm 355 though an orifice 334 in the housing 320.

The bottom tip of the actuator arm 353 may be accessible from an underside of the housing 320.

To transition the syringe assembly 300 from a locked configuration to an unlocked configuration, an individual may exert an upward force on the bottom tip of the actuator arm 353, thereby causing upward deflection of the lock 354. For example, the individual may user his or her finger to push upward on the bottom tip of the actuator arm 353, thereby deflecting the lock 354. Upward deflection of the lock 354 may allow the adaptor 330 to clear the downward protrusion 356 of the lock 354, thereby allowing separation of the syringe barrel 310 from the housing 320.

Figure 21:
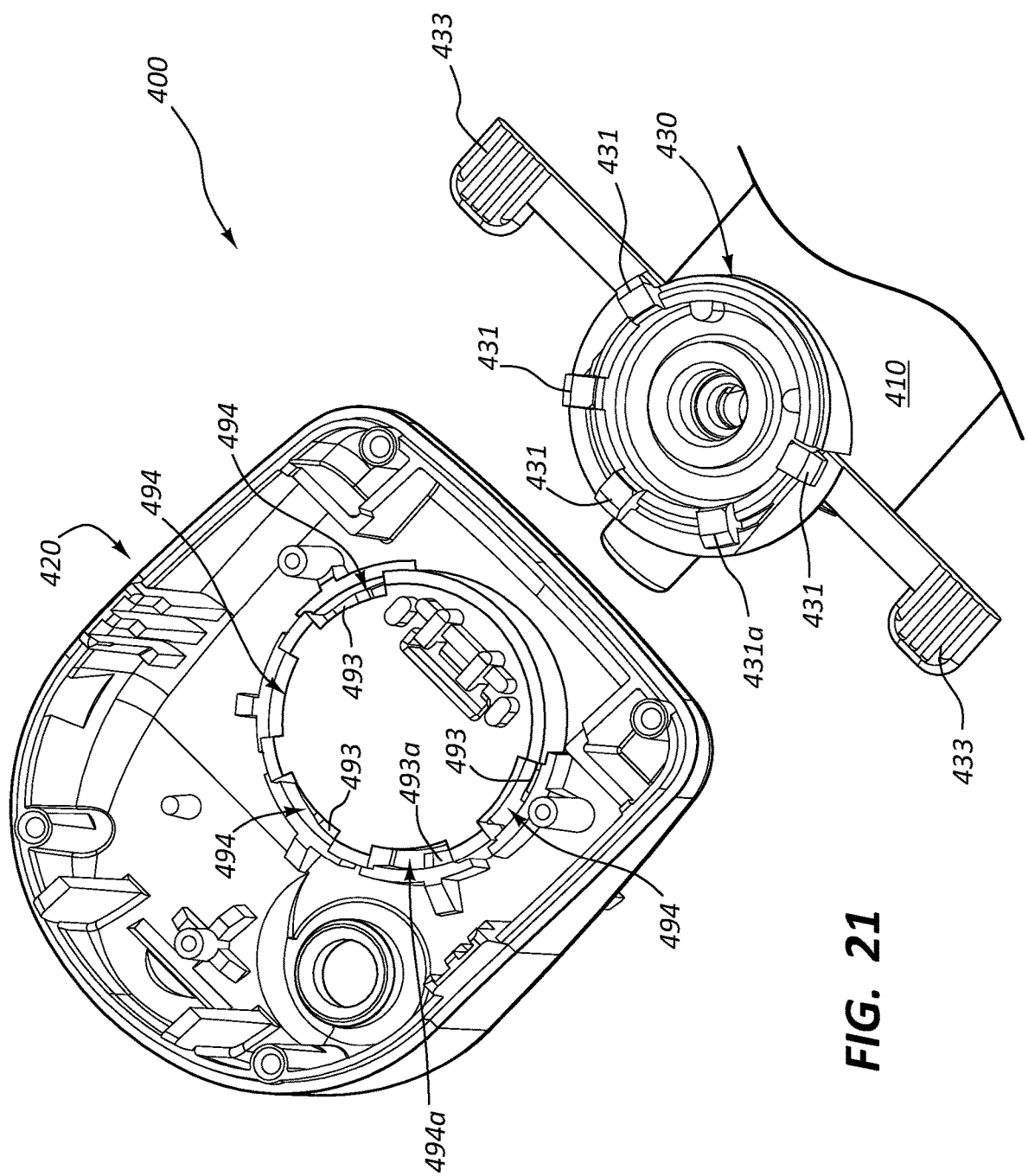
FIG. 21 is a perspective view of a portion of a syringe assembly, according to another embodiment, in which the housing is uncoupled from the syringe barrel.
Figure 22:
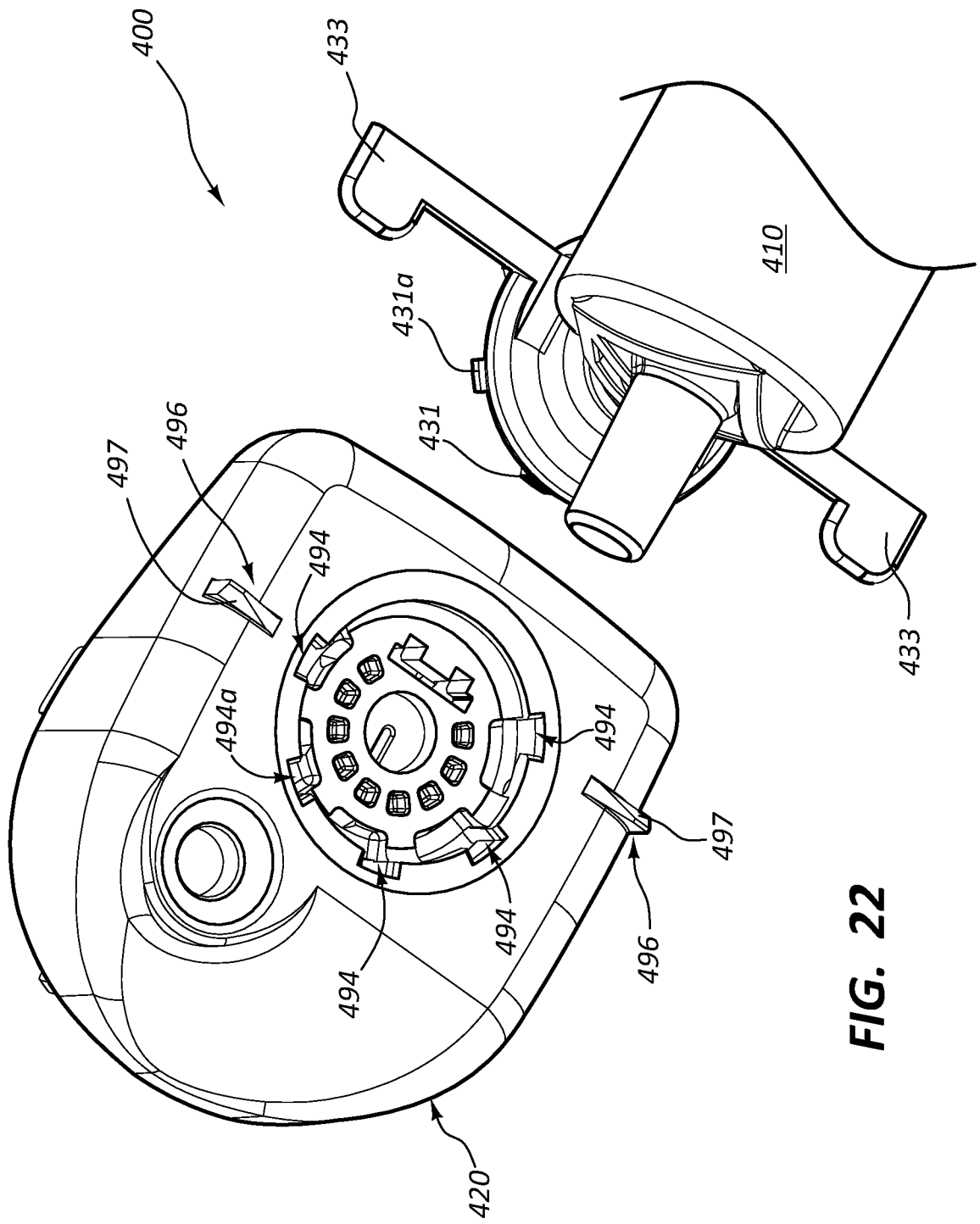
FIG. 22 is a perspective bottom view of a portion of the syringe assembly of FIG. 21, with the housing uncoupled from the syringe barrel.
Figure 23:
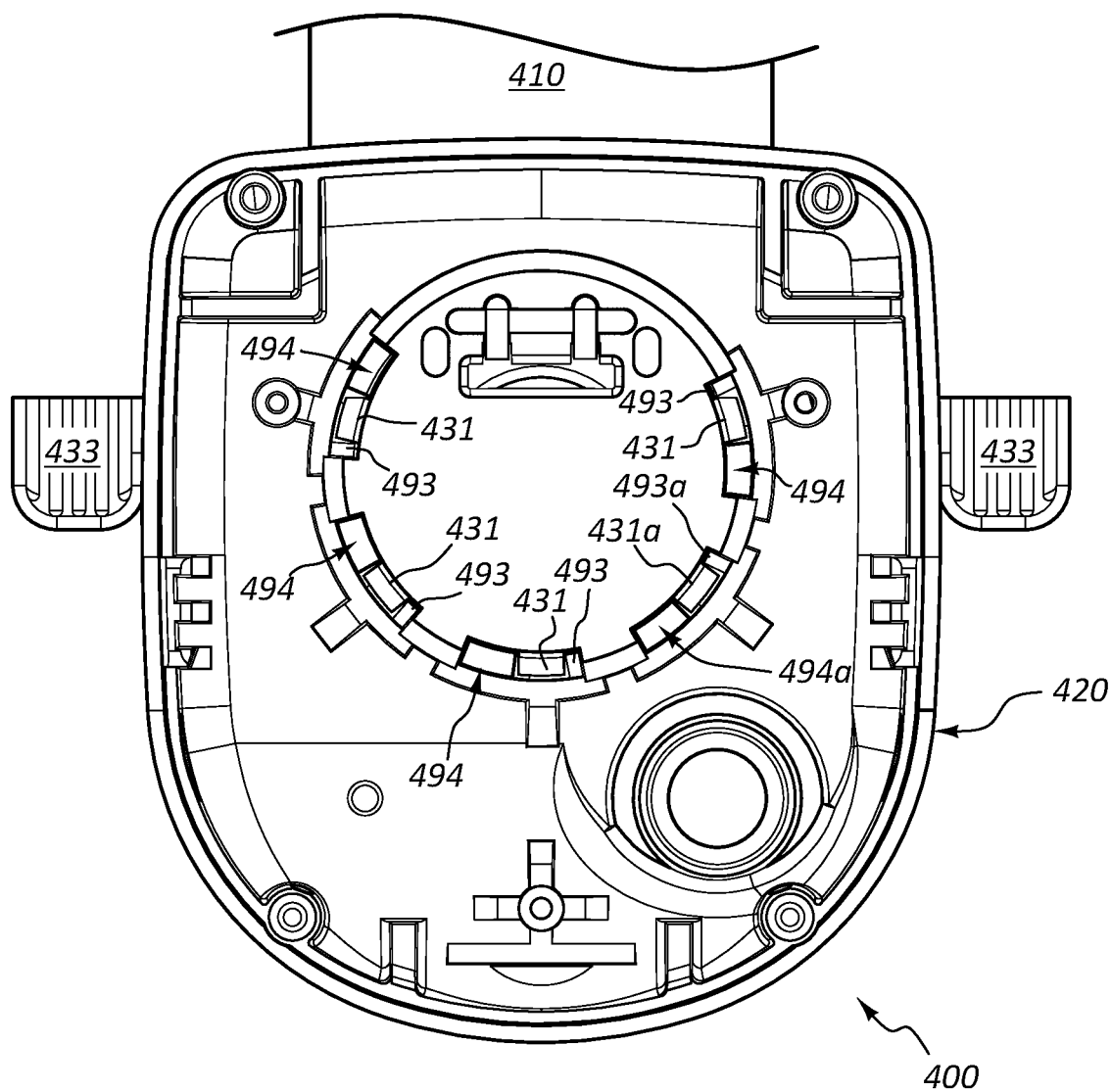
FIG. 23 is a top view of a portion of the syringe assembly of FIG. 21 with the housing coupled to the syringe barrel.
Figure 24:
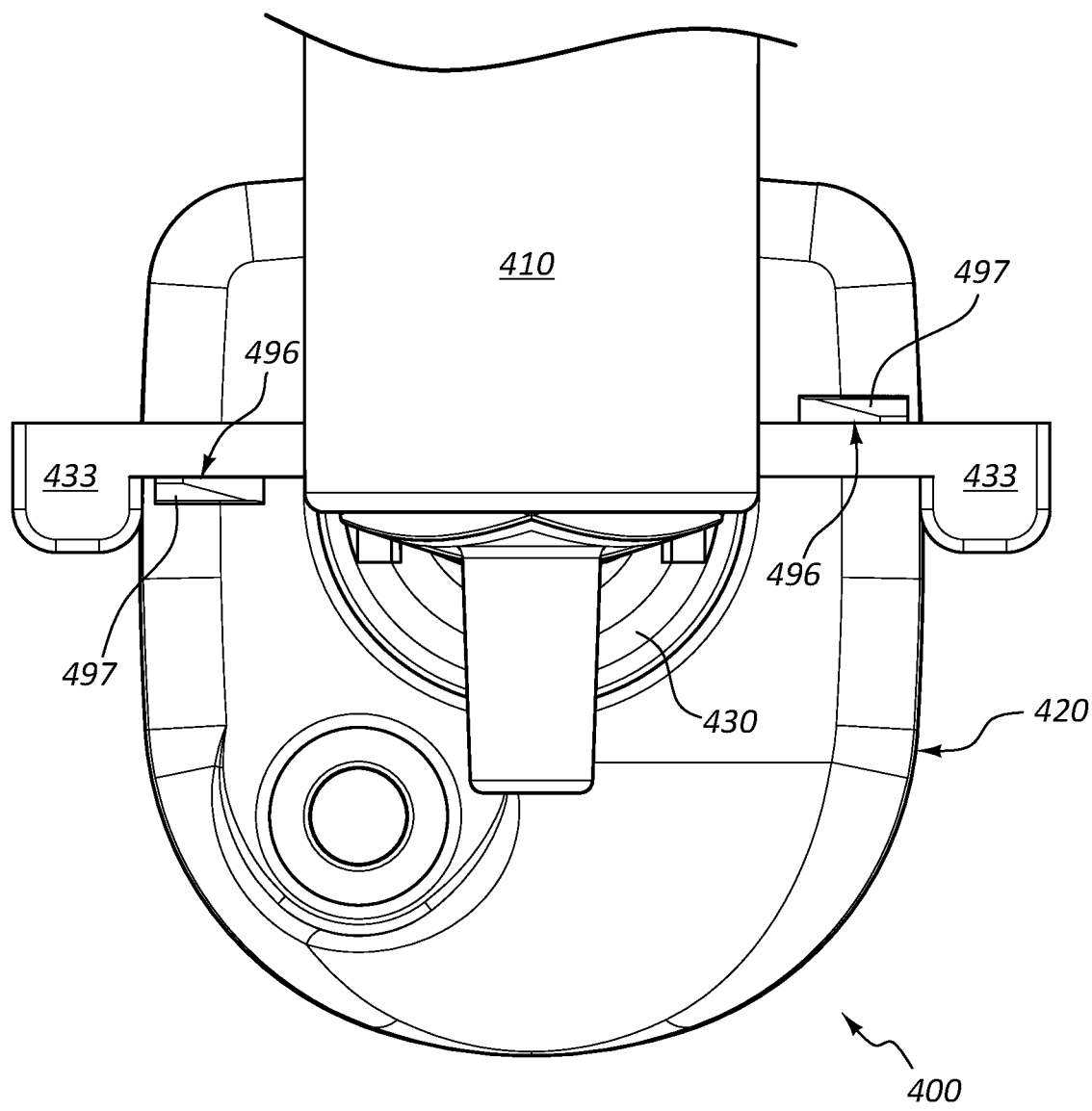
FIG. 24 is a bottom view of a portion of the syringe assembly of FIG. 21 with the housing coupled to the syringe barrel.

FIGS. 21-24 depict a syringe assembly 400, according to another embodiment. More particularly, FIG. 21 provides a perspective view showing an upper side of a distal portion of the syringe assembly 400 in which the housing 420 is uncoupled from the syringe barrel 410. FIG. 22 provides a perspective view showing an underside of a distal portion of the syringe assembly 400 with the housing 420 uncoupled from the syringe barrel 410. FIGS. 23 and 24 provide top and bottom views, respectively, of the syringe assembly 400 in an assembled (i.e., locked) state. In each of FIGS. 21-24, various components, such as the upper portion of the housing, the display screen, the circuit board, the actuator, the pressure transducer, the elastomeric connector, the power sources, etc., have been removed for clarity.

As shown in FIGS. 21-24, the syringe barrel 410 may rotationally couple to the housing 420. For example, the syringe assembly 400 may include an adaptor 430 that is coupled to the syringe barrel 410. The adaptor 430 may include a plurality of outthrusts 431 that extend radially outward from a portion of the adaptor 430. The adaptor 430 may further include a plurality of arms 433 that extend radially outward from the remainder of the adaptor 430 to extend beyond the ends of the plurality of outthrusts 431.

The housing 420 may include a plurality of grooves 494 and a plurality of retaining walls 496. Each groove 494 of the plurality of grooves 494 may be configured to engage with a corresponding outthrust 431 of the adaptor 430. Similarly, each retaining wall 496 may be configured to engage with a corresponding arm 433 of the adaptor 430.

To couple the adaptor 430 to the housing 420, the outthrusts 431 may be aligned with and inserted into the grooves 494 (e.g., outthrust 431a may be aligned with and inserted into groove 494a). The adaptor 430 (and the syringe barrel 410 coupled thereto) may then be rotated (e.g., in a counterclockwise direction as viewed from above) such that each outthrust 431 rests on a ledge 493 within the grooves 494. For example, the outthrust 431a may rest on the ledge 493a within the groove 494a. As the adaptor 430 is rotated, the arms 433 of the adaptor 430 may contact a sloped face 497 of the retaining wall 496, thereby deflecting downward to allow the arms 433 to pass from one side of the retaining wall 496 to the other. The side of the retaining wall 496 that is opposite the sloped face 497 may prevent rotation in the opposite direction (e.g., clockwise as viewed from above), thereby also preventing uncoupling of the adaptor 430 from the housing 420.

To uncouple the adaptor 430 from the housing 420, the user may force the arms in a downward direction (e.g., into the page of FIG. 23). Such force may deflect the arms in a downward direction or cause the arms to snap off of the remainder of the adaptor 430, thereby allowing rotation of the adaptor 430 relative to the housing 420 to uncouple the adaptor 430 from the housing 420.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A syringe assembly comprising:
    an elongate syringe barrel defining a fluid reservoir;
    an adaptor coupled to the elongate syringe barrel;
    a housing coupled to the adaptor;
    a lock coupled to the housing;
    a pressure transducer;
    an aperture that extends through a wall of the elongate syringe barrel such that the fluid reservoir of the elongate syringe barrel is in fluid communication with the pressure transducer; and
    a key,
    wherein the syringe assembly is configured to transition from a locked configuration in which the lock prevents movement of the adaptor relative to the housing to an unlocked configuration in which the adaptor is free to move relative to the housing, and
    wherein the key is configured to extend through an orifice in the housing to displace the lock, thereby transitioning the syringe assembly from the locked configuration to the unlocked configuration.

2. The syringe assembly of claim 1, wherein the syringe assembly is configured to prevent complete withdrawal of the key from the housing.

3. The syringe assembly of claim 1, wherein the key comprises an elongate shaft, the elongate shaft comprising a tip configured to displace the lock.

4. The syringe assembly of claim 3, wherein:
the key further comprises a hub and a plurality of arms;
the elongate shaft extends in a first direction from the hub; and
each arm of the plurality of arms extends in a second direction from the hub toward a display screen within the housing, wherein the second direction differs from the first direction.

5. The syringe assembly of claim 4, wherein the housing comprises one or more catches that are configured to:
allow at least partial insertion of the key into the housing such that the plurality of arms are disposed proximal of the one or more catches; and
prevent complete withdrawal of the key from the housing once the plurality of arms are disposed proximal of the one or more catches.

6. The syringe assembly of claim 1, wherein the housing comprises one or more barrier walls that are configured to limit movement of the key in a proximal direction.

7. The syringe assembly of claim 1, wherein the lock comprises a protrusion having a surface that is angled such that proximal displacement of the key causes the key to contact the surface of the protrusion, thereby displacing the lock to transition the syringe assembly from the locked configuration to the unlocked configuration.

8. The syringe assembly of claim 1, wherein:
the adaptor comprises a channel; and
the key extends through at least a portion of the channel of the adaptor.

9. The syringe assembly of claim 1, wherein the lock is disposed inside of the housing.

10. The syringe assembly of claim 1, wherein the adaptor comprises a plurality of flanges, wherein each flange of the plurality of flanges is in contact with the housing.

11. The syringe assembly of claim 1, further comprising a circuit board and a display screen, wherein the circuit board and the display screen are each disposed within the housing.

12. The syringe assembly of claim 1, wherein the pressure transducer is disposed between the adaptor and the lock.

13. A method of separating components of a pressure-sensing inflation device, the method comprising:
obtaining an inflation device comprising:
an elongate syringe barrel defining a fluid reservoir;
an adaptor coupled to the elongate syringe barrel;
a housing coupled to the adaptor, wherein the housing at least partially encloses one or more of a circuit board and a display screen;
a lock coupled to the housing;
a pressure transducer;
an aperture that extends through a wall of the elongate syringe barrel such that the fluid reservoir of the elongate syringe barrel is in fluid communication with the pressure transducer; and
a key,
wherein the inflation device is configured to transition from a locked configuration in which the lock prevents movement of the adaptor relative to the housing to an unlocked configuration in which the adaptor is free to move relative to the housing, and
wherein the key is configured to extend through an orifice in the housing to displace the lock, thereby transitioning the syringe assembly from the locked configuration to the unlocked configuration,
moving the key toward the lock such that the key displaces the lock; and
separating the housing from the syringe barrel.

14. The method of claim 13, wherein moving the key toward the lock comprises at least partially inserting the key into the housing.

15. The method of claim 13, wherein the lock is coupled to and at least partially disposed within the housing.

16. The method of claim 13, wherein:
the key comprises a hub and an elongate shaft that extends from the hub; and
moving the key toward the lock comprises pushing directly onto the hub of the key.

17. The method of claim 13, further comprising sending one or more of the circuit board, the display screen, and the housing to a refurbisher after the syringe barrel has been separated from the housing.

18. The method of claim 13, further comprising removing one or more of the circuit board and the display screen from the housing after the housing has been separated from the syringe barrel.

19. The method of claim 13, wherein the lock comprises a surface that is angled such that moving the key toward the lock causes the key to contact the surface and displace the lock.

* * * * *